United States Patent [19]

Harata et al.

[11] 4,424,508

[45] Jan. 3, 1984

[54] MOISTURE SENSITIVE ELEMENT

[75] Inventors: Mituo Harata, Kawasaki; Masaki Katsura, Yokosuka; Shigeki Uno, Kawasaki; Hideaki Hiraki, Kawasaki; Masayuki Shiratori, Kawasaki, all of Japan

[73] Assignee: Tokyo Shibaura Denki Kabushiki Kaisha, Kanagawa, Japan

[21] Appl. No.: 291,761

[22] Filed: Aug. 10, 1981

[30] Foreign Application Priority Data

| Aug. 8, 1980 [JP] | Japan | 55-108242 |
| Aug. 15, 1980 [JP] | Japan | 55-111608 |
| Aug. 15, 1980 [JP] | Japan | 55-111613 |
| Aug. 15, 1980 [JP] | Japan | 55-111615 |
| Aug. 15, 1980 [JP] | Japan | 55-111619 |

[51] Int. Cl.³ .............................................. H01L 7/00
[52] U.S. Cl. .................................................... 338/35
[58] Field of Search ................. 338/35; 73/335, 336.5; 422/98; 340/602

[56] References Cited

U.S. PATENT DOCUMENTS 4,052,691 10/1977 Nagano et al. ........................ 338/35

FOREIGN PATENT DOCUMENTS 54-31836 10/1979 Japan .
55-49705 12/1980 Japan .

Primary Examiner—C. L. Albritton
Attorney, Agent, or Firm—Cushman, Darby & Cushman

[57] ABSTRACT

A moisture sensitive element for detecting humidity variations through sensing variations in electric resistance using a porous metal oxide ceramic. At least either phorphorus or sulfur is incorporated in and supported by the porous metal oxide ceramic with the phosphorus or sulfur being applied in either a pure or oxide form.

17 Claims, 17 Drawing Figures

MOISTURE SENSITIVE ELEMENT

BACKGROUND OF THE INVENTION

The present invention relates to a moisture sensitive element of the type which detects variations in humidity with electric resistance.

Moisture sensitive elements which detect variations in humidity by sensing variations of electric signals are used as moisture sensors in automatic humidity control apparatus such as room air conditioners.

One known type of moisture sensor is described, for example, in Japanese Pat. Publications No. 31836/79 and No. 49705/80. It is comprised of an insulative substrate on which a pair of electrodes are disposed, and moisture located between the electrodes will be detected This sensor, however, cannot detect delicate variations of humidity in the surrounding atmosphere.

Another type of prior art moisture sensor comprises a porous metal oxide ceramic plate and a pair of electrodes formed on the same surface or on opposite surface of the ceramic plate. This type of the sensor relies on the excellent hygroscopicity generally exhibited by the metal oxide ceramic. The metal oxide ceramic exhibits significant variation in electric resistance in response to the variation of humidity in the surrounding atmosphere. It is supposed that the variation in electric resistance of the metal oxide ceramic is caused by the movement of protons in the $H_2O$ molecule adsorbed on the surface and on the wall of porosity of the metal oxide ceramic.

However, the humidity-resistance characteristics of this moisture sensor change as time passes because of the adsorption of contaminants such s oil mist, powdered dust, miscellaneous gases and so on onto and into the ceramic as well as the chemisorption occurring between the metal oxide ceramic and part of $H_2O$ molecule adsorbed thereon. In the worst case the moisture sensor would not even exhibit humidity-resistance characteristics.

To eliminate the above-mentioned defect, a method which heats the ceramic at a high temperature so as to desorb the oil mist, powdered dust, miscellaneous gases and $H_2O$ molecule from the ceramics was employed.

In this method, however, the effect of heating is not enough when the temperature of heat is less than 400° C. Therefore, a great deal of electric power is required to effectively heat the moisture sensor and it is not efficient to apply this method to general electronic control circuits. Further, the material disposed around or on which the moisture sensor is mounted must be comprised of an incombustible material. Still further, the moisture sensitive element has to be heated every 30–60 minutes so as to desorb the contaminants. Further, since the moisture sensor cannot be operated during the heating and cooling process, it cannot monitor the humidity continuously if heating is used to remove contaminants.

SUMMARY OF THE INVENTION

Accordingly, it is an object of this invention to provide a moisture sensitive element in which the humidity-resistance characteristics do not significantly change as time passes.

In accordance with the preferred embodiment of this invention, the moisture sensitive element includes an improved moisture sensing element which exhibits significantly better and more consistent response in electric resistance variations in response to variations in relative humidity. A predetermined amount of phosphorus or sulfur is incorporated into the porous metal oxide ceramic and adhered thereto and is thus supported by the ceramic material. The phosphorus or sulfur can be applied either in a pure form or an oxide form. Further, the moisture sensitive element made according to this composition exhibits stable characteristics even over a relatively long lapse of time.

BRIEF DESCRIPTION OF THE DRAWINGS

This invention can be more fully understood from the following detailed description when taken in connection with reference to the accompanying drawing, in which.

DESCRIPTION OF THE PREFERRED EXEMPLARY EMBODIMENTS

Figure 1A:
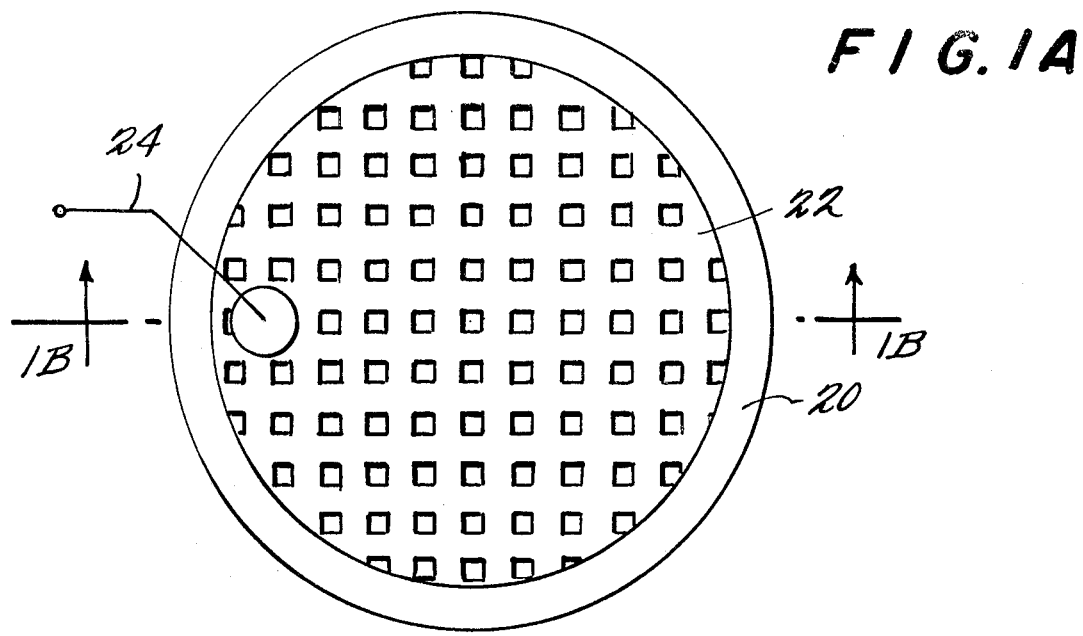
FIG. 1A shows a plan view of a preferred embodiment of the invention.
Figure 1B:
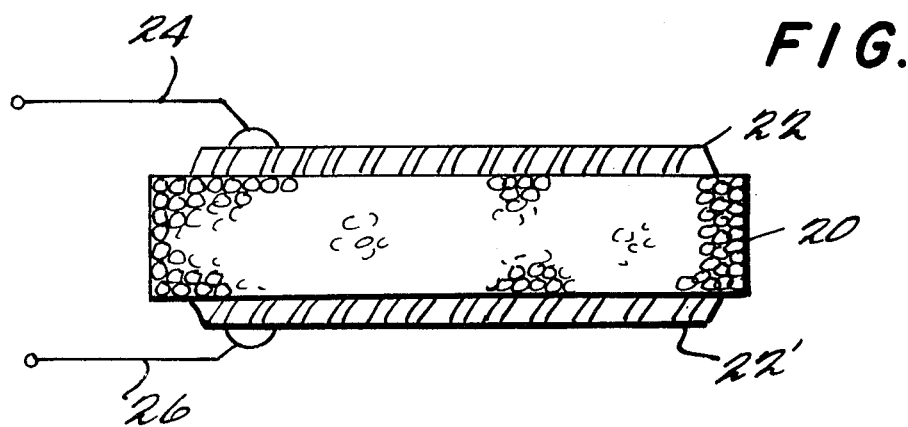
FIG. 1B shows a section of the device taken along the line 1B—1B of FIG. 1A looking in the direction of the arrows.

This invention is based on the discovery that the humidity-resistance characteristics of the moisture sensitive element comprised of the porous metal oxide ceramic on which at least either phosphorus (hereinafter P) or sulfur (hereinafter S) is supported, at least in a pure form or in an oxide form does not significantly change even after a long period of time in comparison with its initial characteristics.

It is not fully understood why the moisture sensitive element of the present invention shows such an excellent retention of its characteristics but it is assumed that the surface of the metal oxide ceramic is reformed to a stable property with respect to moisture.

In the moisture sensitive element of the present invention, the amount of P or S supported in pure form i.e., elemental phosphorus or sulfur, is present in the range of about 0.1 to about 2.0 percent by weight. However, the phosphorus or sulfur may also be in the form of an oxide. Further, both phosphorus and sulphur can be combined and incorporated into or supported on the ceramic substrate and in this instance, as well, the amount of the combination of phosphorus and sulphur can also range from about 0.1 to about 2.0 weight percent. However, when the amount of P or S supported is less than about 0.1 weight percent, the humidity-resistance characteristics are not improved because the amount of adsorption of P or S on the surface of the ceramic is not sufficient. Likewise, when the amount of P or S supported is in excess of about 2.0 weight percent, the electric resistance of the moisture sensitive element elevates too high for the measurement of the resistance.

In the moisture sensitive element of the inventon, any porous metal oxide ceramic having the humidity-resistance characteristics may be employed. For example, $ZnO$, $Fe_2O_3$, $SnO_2$, $MgO$, $Cr_2O_3$, $BaO$, $TiO_2$, $Fe_3O_4$, $MgO.Cr_2O_3$, $BaO.TiO_2$ or $MnO.Fe_2O_3$, or another compounded oxide which other oxide is added to the above mentioned oxide is usually used.

The following compounded oxides containing $ZnO$ as the main element exhibit excellent humidity-resistance characteristics when at least either P or S is supported by them. The compounded oxide comprises about 70 to about 99 mole percent of $ZnO$ and about 1 to about 30 mole percent of at least one material selected from the group consisting of $MgO$, $CaO$, $CoO$ and $MnO$, about 40 to about 99 mole percent of $ZnO$ and about 1 to about 60 mole percent of at least one material selected from the group consisting of $TiO_2$, $SnO_2$, $ZrO_2$ and $SiO_2$, about 60 to about 90 mole percent of $ZnO$ and about 10 to about 40 mole percent of at least either $WO_3$ or $MoO_3$, about 60 to about 99 mole percent of $ZnO$ and about 1 to about 40 mole percent of at least either $Cr_2O_3$ or $Fe_2O_3$, or about 85 to about 95 mole percent of $ZnO$ and about 5 to about 15 mole percent of $V_2O_5$.

The following compounded oxides containing $SnO_2$ as the main element also exhibit excellent humidity-resistance characteristics when at least either P or S is supported by them. The compounded oxide is comprised of about 50 to about 99.9 mole percent of $SnO_2$ and about 0.1 to about 50 mole percent of at least one material selected from the group consisting of $MgO$, $CaO$, $CoO$, $MnO$, $SrO$, $NiO$ and $CuO$, about 60 to about 99.9 mole percent of $SnO_2$ and about 0.1 to about 40 mole percent of at least either $WO_3$ or $MoO_3$, about 60 to about 99.9 mole percent of $SnO_2$ and about 0.1 to about 40 mole percent of at least one material selected from the group consisting of $Al_2O_3$, $Ga_2O_3$ and $In_2O_3$, or about 75 to about 99.9 mole percent of $SnO_2$ and about 0.1 to about 25 mole percent of at least one material selected from the group consisting of $V_2O_5$, $Nb_2O_5$ and $Ta_2O_5$.

Further, the following compounded oxides containing $Cr_2O_3$ as the main element also exhibit excellent humidity-resistance characteristics when either P or S is supported by them. The compounded oxide is comprised of about 30 to about 80 mole percent of $Cr_2O_3$ and about 20 to about 70 mole percent of at least one material selected from the group consisting of $MgO$, $NiO$, $CoO$ and $MnO$, about 40 to about 80 mole percent of $Cr_2O_3$ and about 20 to about 60 mole percent of at least one material selected from the group consisting of $TiO_2$, $SnO_2$, $ZrO_2$ and $SiO_2$, about 60 to about 90 mole percent of $Cr_2O_3$ and about 10 to about 40 mole percent of at least either $WO_3$ or $MoO_3$, about 70 to about 90 mole percent of $Cr_2O_3$ and about 10 to about 30 mole percent of at least one material selected from the group consisting of $V_2O_5$, $Nb_2O_5$ and $Ta_2O_5$.

When the content of each element in these compounded oxides is out of the above-mentioned range, the electric resistance of the ceramics elevates so high (about over 5000 $K\Omega$) that the variation of electric resistance of the ceramic reduced as compared with the variation of humidity. As a result, the moisture sensitive element cannot be put to practical use. Further, the compounded oxides within the above composition ranges have excellent sintering properties and mechanical strength.

The moisture sensitive element of this invention may be prepared in the following manner. Raw material oxides accurately weighed out in prescribed amount are mixed together with, for example, ethyl alcohol or ethylene glycol in a ball mill and then dried. The mixed oxides are calcined at 700 degrees to 1000 degrees C. as occasion demands and pulverized into powder. The powder thus obtained is mixed with a binder such as polyvinyl alcohol (PVA) and liquid paraffin, and the mixture is shaped under a pressure of about 500 to 2000 $kg/cm^2$, into, for example, a plate having a width of 10 mm, a length of 20 mm and a thickness of 1 mm. The plate is sintered at about 1000 degrees to 1300 degrees C. generally in air. During sintering, it is kept at a maximum temperature for 0.5 to 2 hours.

In this invention, the ceramic has to have a porous structure and preferably the integral distribution of the porosity of over 10 Angstroms in size is 0.1 to 0.002 cc/g to the weight (g) of the ceramic. Since the porous structure may be obtained under the condition which, for example, the grain size of raw material oxide is 0.1 to 2.0 $\mu m$, the shaping pressure is 500 to 2000 $kg/cm^2$, the sintering temperature, 1000 to 1300 degrees C. and the sintering time is 0.5 to 2 hours.

A pair of electrodes are formed on the same surface or each opposite surface of the ceramic prepared as above by painting a conductive paste such as a gold paste, a platinum paste, a ruthenium oxide paste or a carbon paste on the ceramic and then burning it together. Finally, the pure form and/or oxide form of at least either P or S is supported by the ceramics. Either P or S may be supported by the ceramic in the following manner. A solution containing either P or S is impregnated into the ceramics and then decomposed by heat. Either the pure form or the oxide of either P or S in the solution is retained on the surface of the ceramic or on the walls of pores of the ceramic by the thermal decomposition in the heat treatment. The solution comprises, for example, organic phosphorous acid solution such as triethyl phosphate, trimethyl phosphate, tributyl phosphate, tri-p-cresyl phosphate and tri-o-cresyle phosphate, inorganic phosphorous acid solution such as phosphoric acid, phosphorous acid and pyrophosphoric acid, or organic sulfur solution such as ethyl sulfide, vinyl sulfide, phenyl sulfide, benzyl sulfide, methyl sulfide, triethylphosphine sulfide and diethyl sulfide. These solutions may be mixed or used singly.

It is preferable that the impregnation of the solution is carried out under a reduced pressure or a vacuum to uniformly impregnate the solution into even the center of the ceramic.

The ceramic thus obtained is thereafter heated. The temperature must be about the temperature of thermal decomposition of the solution. However, the upper limit of the temperature is 700 degrees C., preferably 550 degrees C. When the temperature is over 700 degrees C. the effect of supporting is not enough because P or S supported by the ceramic is vaporized or coagulated. Conversely, when the temperature is too low, the effect of supporting is not also enough because P or S cannot adhere to the ceramic.

The moisture sensitive element of the present invention also may be produced by supporting P or S by a metal oxide layer formed on a substrate such as an alumina or magnesia by the thick film method, for example, sputtering vacuum evaporation.

The moisture sensitive element of the present invention constructed as above has excellent humidity-resistance characteristics. Namely, the change of the humidity resistance characteristics with passage of time is very small so that continuous and reliable monitoring of humidity is possible.

This invention will be more clearly understood with reference to the following exemplary Examples.

EXAMPLE 1

Powder of ZnO with the particle size of 0.1 to 2.0 $\mu$m was dried at 150 degrees C. for two hours and then mixed with 5 percent polyvinyl alcohol of 8 weight percent for about 20 minutes by mixer. The mixture thus obtained was placed in a cylinder and a pressure of 1000 kg/cm$^2$ at about 25 degrees C. was applied to make a ceramic disc.

The ceramic disc was heated in an electric furnace at 1100 degrees C. for an hour and then ground by silicon abrasives of #3000. Thus, a ceramic disc having a diameter of 10 mm and a thickness of 1.0 mm was obtained as shown in FIG. 1A at 20. This ceramic disc 20 had 0.050 cc/g of the integral distribution of pores of over 37 Angstroms in size. A gold paste was spread on both surfaces of disc 20 and then gold mesh type electrodes 22 and 22' having the diameter of 8.0 mm were formed by baking at 750 degrees C.

The ceramic disc was steeped in triethyl phosphate including P of 18 weight percent at $10^{-3}$ Torr for 2 hours and was dried at 100 degrees C. for an hour. The ceramic disc thus obtained was heated in an electric furnace at 550 degrees C. for half an hour. The moisture sensitive element prepared as above was found in the chemical analysis that P supported by the ceramic was 0.8 weight percent to the weight of the ceramic.

Figure 2:
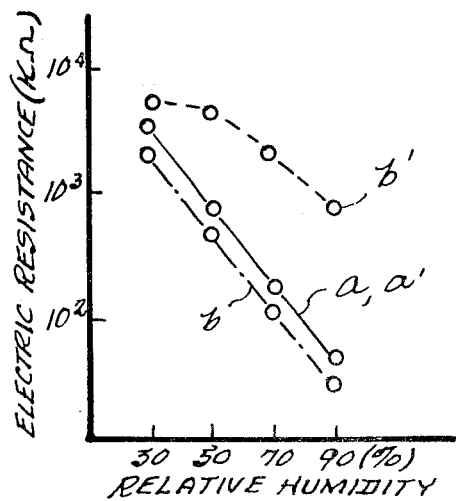
FIG. 2 illustrates a graph showing relationship between the humidity and electric resistance of the moisture sensitive element according to the present invention which the phosphorus is supported by a ZnO ceramics body, and a prior art moisture sensitive element, respectively, in which a and b are the initial values, and a' and b' are the values of 500 hours after.

Copper lead lines 24 and 26 were connected to the gold electrodes 22 and 22', respectively and an impedance measuring circuit was connected to the copper lines. The relationship between relative humidity (percent) and electric resistance (K$\Omega$), which are initial humidity-resistance characteristics, were then measured under a constant temperature and humidity. The result is shown in FIG. 2 and Example 1 of Table 1. The humidity-resistance characteristics were measured again after 500 hours and the result is also shown in FIG. 2 and Example 1 of Table 1. In FIG. 2 curve "a" presents the initial characteristics while curve "a'" presents the characteristics after 500 hours of use.

Table 1 shows the initial electric resistance values $R_1$ and $R_2$ under the relative humidity of 30 percent and 90 percent, respectively, the electric resistance values $R_1'$, and $R_2'$ of 500 hours after under the relative humidity of 30 percent and 90 percent, respectively, and the change rate $(R_1'-R_1)/R_1 \times 100$ and $(R_2'-R_2)/R_2 \times 100$.

As a comparison, the humidity-resistance characteristics of a prior art element formed of ZnO ceramic by which P was not supported are also shown in FIG. 2 and control 1 of Table 1. In FIG. 2a curve "b" presents the initial characteristics and a curve "b'" presents the characteristics of 500 hours after.

As is apparent from the above results, the humidity-resistance characteristics of the prior art element exhibit a great change with passage of time. However, that of the moisture sensitive element of the present invention does not significantly change with passage of time. Therefore, the moisture sensitive element of the present invention has a great reliability when used in continuous monitoring applications.

EXAMPLE 2

A ZnO ceramic disc was made in the same manner as in Example 1. S was supported by the ZnO ceramic disc in the same manner as Example 1 except for use of 35 weight percent ethyl sulfide as an impregnation solution. The moisture sensitive element thus obtained had 0.9 weight percent of S.

In the same manner as Example 1, the humidity-resistance characteristic of the disc initially and after 500 hours were measured. The result was shown in Example 2 of Table 1.

EXAMPLES 3 TO 16

A plurality of moisture sensitive elements, on which either P or S was supported by ceramic discs made of metal oxide shown in EXAMPLES 3 to 16 of Table 1, were manufactured, and several kinds of moisture sensitive elements (controls 2 to 8) on which neither P nor S was supported by the ceramic disc were manufactured. The characteristics of the example elements and control elements were measured and are as shown in Table 1.

As shown in Table 1 and FIG. 2, according to the present invention the rate of moisture sensitive variation is very small so that the continuous and reliable monitoring of humidity is possible.

EXAMPLES 17 TO 23

A plurality of moisture sensitive elements, on which both P and S were supported by the ceramic discs made of the metal oxide shown in EXAMPLES 17 to 23 of Table 2, were made again in the same manner as in Example 1 except that the impregnation solution was changed to a mixture of triethyl phosphate containing P of 18 weight percent and ethyl sulfide containing S of 35 weight percent (mixed rate: 1:1).

The amount of P and S supported by the metal oxide ceramic were equal to each other.

The characteristics of the moisture sensitive elements were measured, and are shown in Table 2.

As Table 2 shows, the rate of electric resistance variation is very small.

EXAMPLE 24

Figure 3:
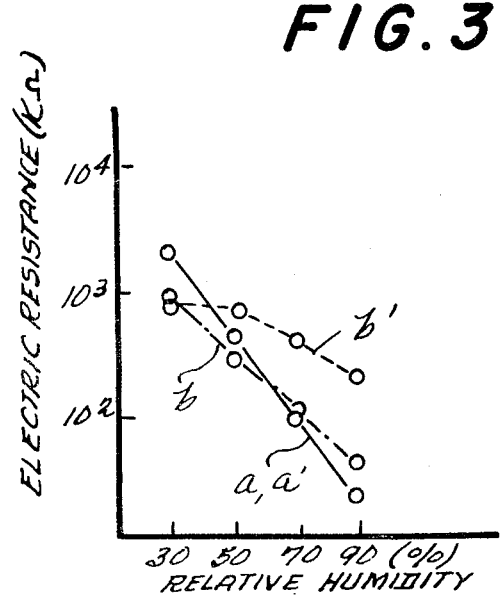
FIG. 3 illustrates a graph showing relationship between the humidity and electric resistance of the moisture sensitive element according to the present invention which the phosphorus is supported by an $Fe_2O_3$ layer, and a prior art moisture sensitive element, respectively, in which a and b are the initial values, and a' and b' are the values of 500 hours after.
Figure 4:
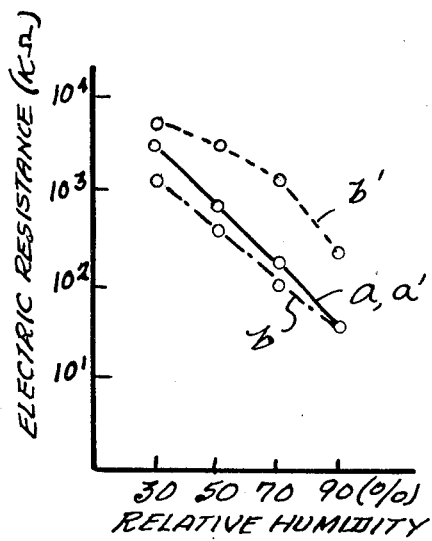
FIGS. 4 to 8, 9 to 12, and 13 to 16 illustrate graphs showing the relationship between the humidity and electric resistance of moisture sensitive elements produced according to the present invention which the phosphorus is supported by a ceramic body having ZnO, $SnO_2$ and $Cr_2O_3$ as a principal component, and prior art moisture sensitive elements, respectively, in which a and b are the initial values, and a' and b' are the values of 1000 hours after.
Figure 5:
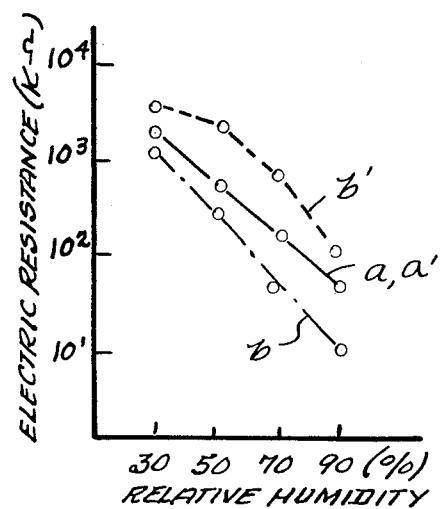
Figure 6:
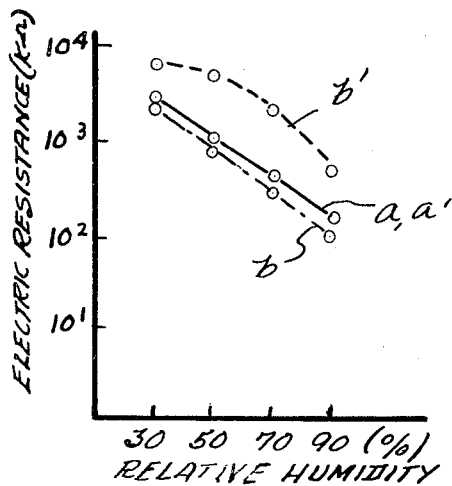
Figure 7:
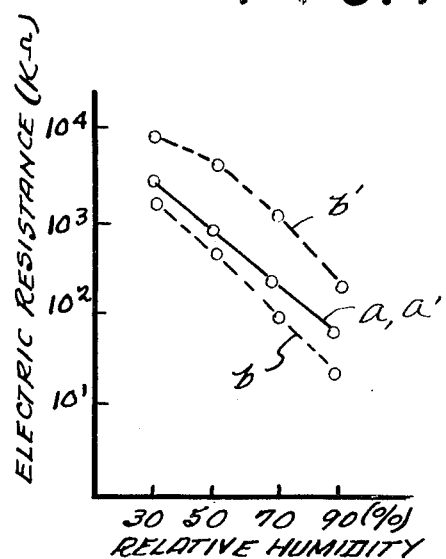
Figure 8:
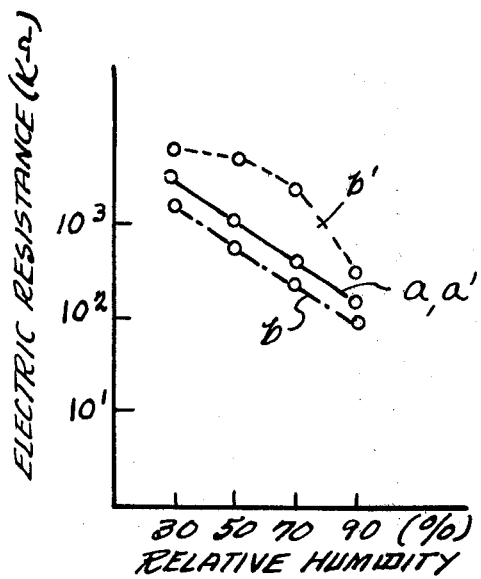
Figure 9:
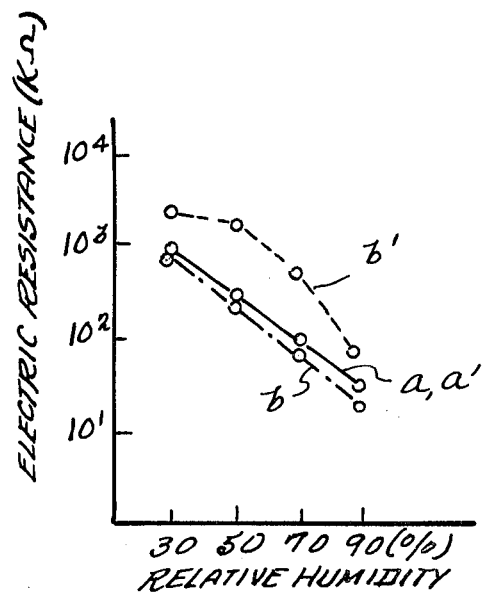
Figure 10:
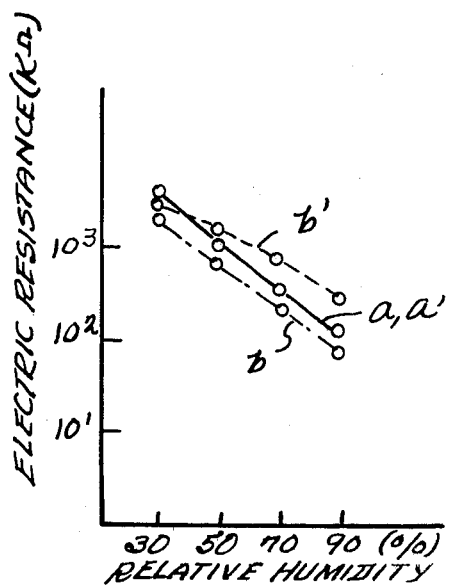
Figure 11:
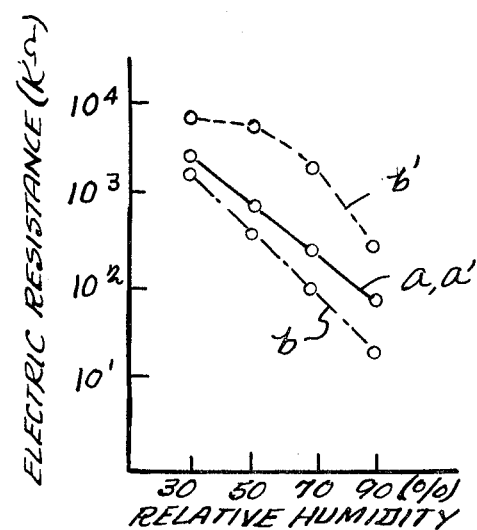
Figure 12:
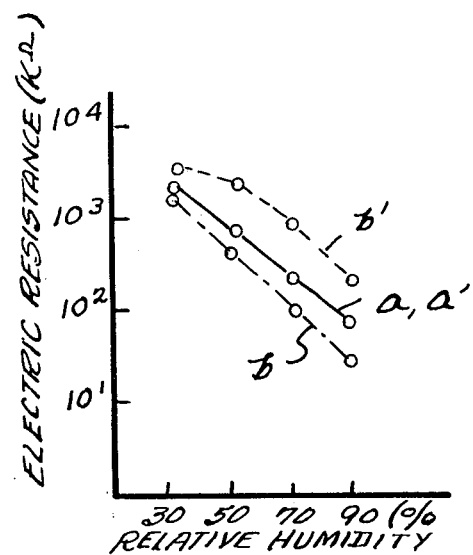
Figure 13:
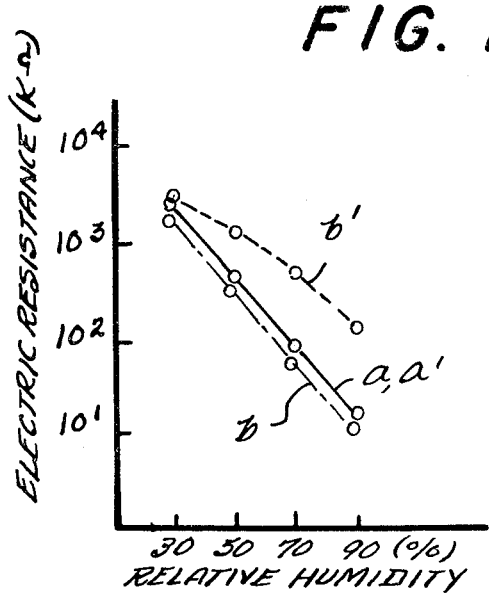
Figure 14:
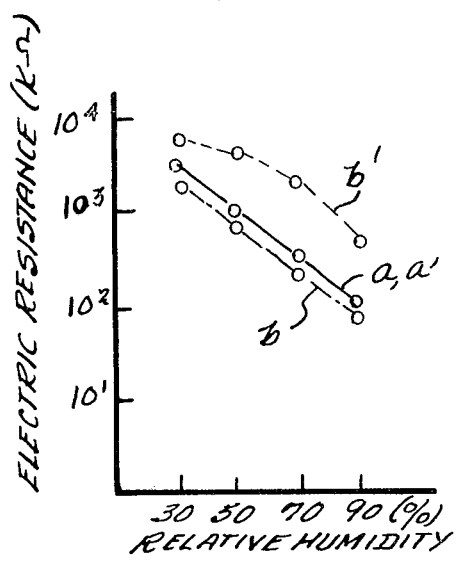
Figure 15:
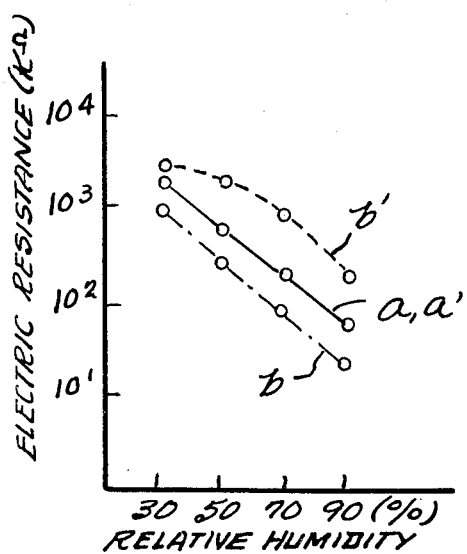
Figure 16:
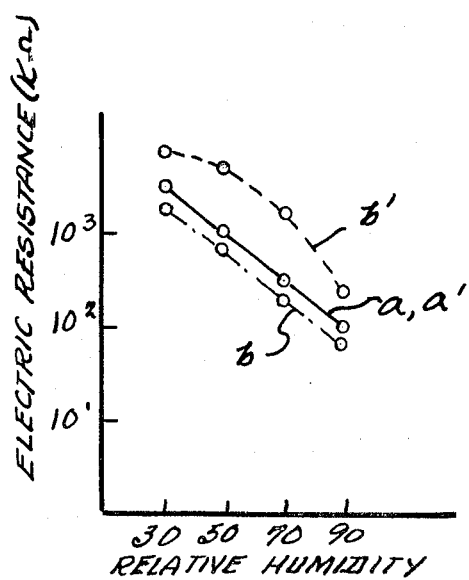

A sintered alumina having a length of 20 mm, a width of 10 mm and a thickness of 0.5 mm was prepared. A pair of interdigital metal electrodes were formed on the sintered alumina. On the thick film type moisture sensitive element thus prepared, P was supported, and the characteristics were measured. The results are set forth in Example 24 of FIG. 3 and Table 3. As a comparison, the characteristics of an element on which P is not supported were measured, and are also shown in control 9 of FIG. 3 and Table 3. As FIG. 3 and Table 3 shows, the rate of moisture sensitive variation of the element of the invention is small.

EXAMPLES 25 TO 132

The moisture sensitive elements, which satisfy the specification as shown in Examples 25 to 132 and controls 10 to 67 of Table 4, 6, 8, 10, 12, 14, 16, 18, 20, 22, 24, 26 and 28, were made in the same manner as in Example 1.

The humidity-resistance characteristics of these moisture sensitive elements were measured, and are shown in Tables 4, 7, 9, 11, 13, 15, 17, 19, 21, 23, 25, 27 and 29 and the characteristics of Examples 25, 34, 46, 52, 59, 63, 74, 83, 92, 100, 109, 117 and 125 and controls 10, 15, 20, 24, 29, 33, 37, 41, 45, 49, 54, 59 and 64 are shown in FIGS. 4 to 16.

From these results it is clear that moisture sensitive elements can be formed using either ZnO, $SnO_2$ or $Cr_2O_3$ as the base element forming the porous metal oxide ceramic on which either P or S was supported. Each form exhibited excellent humidity resistance characteristics and the rate of moisture sensitive variation was very small.

Exemplary structured formed using ZnO, $SnO_2$ and $Cr_2O_3$ as the base material for the porous ceramic are as follows:

(1) ZnO as the porous metal oxide ceramic with various compounded oxides as follows:
   (a) about 70 to about 99 mole percent of ZnO and about 1 to about 30 mole percent of at least one material selected from the group consisting of MgO, CaO, CoO and MnO,
   (b) about 40 to about 99 mole percent of ZnO and about 1 to about 60 mole percent of at least one material selected from the group consisting of $TiO_2$, $SnO_2$, $ZrO_2$ and $SiO_2$,
   (c) about 60 to about 90 mole of ZnO and about 10 to about 40 mole percent of at least either $WO_3$ or $MoO_3$,
   (d) about 60 to about 99 mole percent of ZnO and about 1 to about 40 mole percent of at least either $Cr_2O_3$ or $Fe_2O_3$, or
   (e) about 85 to about 90 mole percent of ZnO and about 5 to about 15 mole percent of $V_2O_5$.

(2) $SnO_2$ as the porous metal oxide ceramic with various compounded oxides as follows:
   (a) about 50 to about 99.9 mole percent of $SnO_2$ and about 0.1 to about 50 mole percent of at least one material selected from the group consisting of MgO, CaO, CoO, MnO, SrO, NiO and CuO,
   (b) about 60 to about 99.9 mole percent of $SnO_2$ and about 0.1 to about 40 mole percent of at least either $WO_3$ or $MoO_3$,
   (c) about 60 to about 99.9 mole percent of $SnO_2$ and about 0.1 to about 40 mole percent of at least one material selected from the group consisting of $Al_2O_3$, $Ga_2O_3$ and $In_2O_3$, or
   (d) about 75 to about 99.5 mole percent of $SnO_2$ and about 0.1 to about 25 mole percent of at least one material selected from the group consisting of $V_2O_5$, $Nb_2O_5$ and $Ta_2O_5$.

(3) $Cr_2O_3$ as the porous metal oxide ceramic with various compounded oxides as follows:
   (a) about 30 to about 80 mole percent of $Cr_2O_3$ and about 20 to about 70 mole percent of at least one material selected from the group consisting of MgO, NiO, CoO and MnO,
   (b) about 40 to about 80 mole percent of $Cr_2O_3$ and about 20 to about 60 mole percent of at least one material selected from the group consisting of $TiO_2$, $SnO_2$, $ZrO_2$ and $SiO_2$,
   (c) about 60 to about 90 mole percent of $Cr_2O_3$ and about 10 to about 40 mole percent of at least either $WO_3$ or $MoO_3$, or
   (d) about 70 to about 90 mole percent of $Cr_2O_3$ and about 10 to about 30 mole percent of at least one material selected from the group consisting of $V_2O_5$, $Nb_2O_5$ and $Ta_2O_5$.

As described above, the moisture sensitive element according to the present invention has the excellent humidity-resistance characteristics and that the rate of moisture sensitive variation is very small.

While in many changes and modifications in the above-described embodiments can, of course, be carried out without departing from the scope of the present invention, that scope is intended to be limited only by the scope of the appended claims.

TABLE 1

| | COMPOSITION OF MOISTURE SENSITIVE ELEMENT | Supporting Material | Amount (wt %) | INITIAL $R_1$ (kΩ) | $R_2$ (kΩ) | 500 HOURS AFTER $R_1'$ (kΩ) | $R_2'$ (kΩ) | RATE OF VARIATION $(R_1' - R_1)/R_1$ (%) | $(R_2' - R_2)/R_2$ (%) |
|---|---|---|---|---|---|---|---|---|---|
| Example 1 | ZnO | P | 0.8 | 3200 | 45 | 3600 | 48 | +12.5 | +6.7 |
| Example 2 | ZnO | S | 0.9 | 1800 | 24 | 2068 | 26 | +14.9 | +8.3 |
| Example 3 | $Fe_2O_3$ | P | 0.6 | 2200 | 30 | 2150 | 29 | −2.3 | −3.3 |
| Example 4 | $SnO_2$ | " | 0.7 | 1250 | 98 | 1290 | 96 | 13.2 | −2.0 |
| Example 5 | $Cr_2O_3$ | " | " | 18300 | 290 | 18000 | 265 | −1.6 | −8.6 |
| Example 6 | $Fe_3O_4$ | " | 0.6 | 1150 | 85 | 1170 | 93 | +1.7 | +9.4 |
| Example 7 | $MgO.Cr_2O_3$ | " | 0.7 | 5100 | 270 | 5100 | 255 | 0 | −5.6 |
| Example 8 | $BaO.TiO_2$ | " | 0.8 | 920 | 38 | 900 | 40 | −2.2 | +5.6 |
| Example 9 | $MnO.Fe_2O_3$ | " | " | 3550 | 720 | 3470 | 680 | −2.3 | −5.6 |
| Example 10 | $Fe_2O_3$ | S | 0.7 | 1580 | 44 | 1660 | 46 | +5.1 | +4.5 |
| Example 11 | $SnO_2$ | " | 0.8 | 875 | 21 | 900 | 22 | 12.9 | 14.8 |
| Example 12 | $Cr_2O_3$ | " | " | 17700 | 205 | 17300 | 195 | 2.3 | −4.9 |
| Example 13 | $Fe_3O_4$ | " | " | 980 | 90 | 1020 | 91 | +4.1 | +1.1 |
| Example 14 | $MgO.Cr_2O_3$ | " | " | 4000 | 250 | 5100 | 265 | +4.1 | +6 |
| Example 15 | $BaO.TiO_2$ | " | 0.9 | 640 | 32 | 610 | 28 | −1.7 | −12.5 |
| Example 16 | $MnO.Fe_2O_3$ | " | " | 3500 | 640 | 3350 | 600 | −4.3 | −6.3 |
| Control 1 | ZnO | — | — | 2100 | 43 | 5200 | 720 | +148 | +1574 |
| Control 2 | $Fe_2O_3$ | — | — | 1300 | 50 | 1100 | 280 | −15.4 | +460 |
| Control 3 | $SnO_2$ | — | — | 980 | 115 | 760 | 195 | −22.4 | +69.6 |
| Control 4 | $Cr_2O_3$ | — | — | >20000 | 230 | >20000 | 1200 | — | +422 |
| Control 5 | $Fe_3O_4$ | — | — | 1070 | 65 | 2120 | 143 | 1981 | +120 |
| Control 6 | $MgO.Cr_2O_3$ | — | — | 5500 | 300 | >20000 | 1000 | >1264 | +233 |
| Control 7 | $BaO.TiO_2$ | — | — | 660 | 23 | 1210 | 85 | +83.3 | +270 |

TABLE 1-continued

| | COMPOSITION OF MOISTURE SENSITIVE ELEMENT | Supporting Material | Amount (wt %) | INITIAL $R_1$ (kΩ) | $R_2$ (kΩ) | 500 HOURS AFTER $R_1'$ (kΩ) | $R_2'$ (kΩ) | RATE OF VARIATION $(R_1' - R_1)/R_1$ (%) | $(R_2' - R_2)/R_2$ (%) |
|---|---|---|---|---|---|---|---|---|---|
| Control 8 | $MnO \cdot Fe_2O_3$ | — | — | 4350 | 1020 | 5600 | 3100 | +28.7 | +204 |

TABLE 2

| | COMPOSITION OF MOISTURE SENSITIVE ELEMENT | RATIO OF P & S | SUPPORTING AMOUNT (wt %) | INITIAL $R_1$ (kΩ) | $R_2$ (kΩ) | 500 HOURS AFTER $R_1'$ (kΩ) | $R_2'$ (kΩ) | RATE OF THE VARIATION $(R_1' - R_1)/R_1$ (%) | $(R_2' - R_2)/R_2$ (%) |
|---|---|---|---|---|---|---|---|---|---|
| Example 17 | ZnO | 1 | 0.8 | 2800 | 40 | 2850 | 43 | 11.8 | 17.5 |
| Example 18 | $Fe_2O_3$ | " | 0.7 | 2300 | 45 | 2150 | 41 | −6.5 | −8.9 |
| Example 19 | $SnO_2$ | " | " | 1070 | 85 | 1200 | 78 | 112.1 | −8.2 |
| Example 20 | $Cr_2O_3$ | " | " | 16000 | 350 | 14300 | 310 | −10.6 | −11.4 |
| Example 21 | $Fe_3O_4$ | " | " | 1200 | 80 | 1310 | 85 | 19.2 | +6.3 |
| Example 22 | $MgO \cdot Cr_2O_3$ | " | 0.8 | 6200 | 215 | 6450 | 220 | +4.0 | +2.3 |
| Example 23 | $MnO \cdot Fe_2O_3$ | " | " | 4030 | 920 | 3900 | 830 | −3.2 | −9.8 |

TABLE 3

| | COMPOSITION OF MOISTURE SENSITIVE ELEMENTS | SUPPORTING MATERIAL | AMOUNT (Wt %) | INITIAL $R_1$ (kΩ) | $R_2$ (kΩ) | 500 HOURS AFTER $R_1'$ (kΩ) | $R_2'$ (kΩ) | RATE OF THE VARIATION $(R_1' - R_1)/R_1$ (%) | $(R_2' - R_2)/R_2$ (%) |
|---|---|---|---|---|---|---|---|---|---|
| Example 24 | $Fe_2O_3$ | P | 0.6 | 2100 | 25 | 2300 | 27 | +9.5 | +8.0 |
| Control 9 | $Fe_2O_3$ | — | — | 880 | 41 | 780 | 200 | −11.4 | +388 |

TABLE 4

| | COMPOSITION | | | | | BINDER | SHAPING PRESSURE (Kg/cm²) | SINTERING TEMPERATURE (°C.) | SINTERING TIME (hr) | SOLUTION | CONSISTENCY (wt %) | HEATING TEMPERATURE (°C.) |
|---|---|---|---|---|---|---|---|---|---|---|---|---|
| | ZnO | CaO | CoO | MgO | MnO | | | | | | | |
| Example 25 | 86.5 | 13.5 | — | — | — | PVA | 1,000 | 1100 | 2 | Triethyl Phosphate | 18 | 550 |
| Example 26 | " | " | — | — | — | " | " | " | " | Ethyl Sulfide | 35 | " |
| Example 27 | 99.4 | 0.6 | — | — | — | " | " | " | " | Triethyl Phosphate | 18 | 550 |
| Example 28 | 93.5 | 6.5 | — | — | — | " | " | " | " | " | " | " |
| Example 29 | 78.8 | 21.2 | — | — | — | " | " | " | " | " | 20 | " |
| Example 30 | 89.0 | — | — | 11.0 | — | " | " | " | " | " | " | " |
| Example 31 | 85.0 | — | 9.8 | 5.2 | — | " | " | " | " | " | " | " |
| Example 32 | 77.6 | 6.9 | 5.1 | 5.5 | 4.9 | " | " | " | " | " | " | " |
| Example 33 | 89.0 | — | — | 11.0 | — | " | " | " | " | Ethyl Sulfide | 35 | " |
| Control 10 | 86.5 | 13.5 | — | — | — | " | " | " | " | — | — | |
| Control 11 | 99.7 | 0.3 | — | — | — | " | " | " | " | Triethyl Phosphate | 18 | 550 |
| Control 12 | 70.5 | 29.5 | — | — | — | " | " | " | " | " | " | " |
| Control 13 | 86.5 | 13.5 | — | — | — | " | " | " | " | " | " | 700 |
| Control 14 | 89.0 | — | — | 11.0 | — | " | " | " | " | " | " | " |

TABLE 5

| | COMPOSITION | | | | | SUPPORTING MATERIAL | AMOUNT (wt %) | INITIAL $R_1$ (KΩ) | $R_2$ (KΩ) | 1,000 Hours After $R_1'$ (KΩ) | $R_2'$ (KΩ) |
|---|---|---|---|---|---|---|---|---|---|---|---|
| | ZnO | CaO | CoO | MgO | MnO | | | | | | |
| Example 25 | 8.0 | 20 | — | — | — | P | 0.9 | 3200 | 45 | 3700 | 49 |
| Example 26 | " | " | — | — | — | S | 1.0 | 4900 | 87 | 5100 | 91 |
| Example 27 | 99.0 | 1.0 | — | — | — | P | 0.9 | 4600 | 390 | 4800 | 420 |
| Example 28 | 90 | 10 | — | — | — | " | " | 2700 | 190 | 2900 | 220 |
| Example 29 | 70 | 30 | — | — | — | " | " | 6500 | 240 | 6800 | 280 |
| Example 30 | 80 | — | — | 20 | — | " | " | 4300 | 82 | 4500 | 84 |
| Example 31 | " | — | 10 | 10 | — | " | " | 3700 | 67 | 3900 | 70 |
| Example 32 | 70 | 10 | 5 | " | 5 | " | " | 7700 | 310 | 7900 | 330 |
| Example 33 | 80 | — | — | 20 | — | S | 1.0 | 5200 | 69 | 5300 | 71 |
| Control 10 | " | 20 | — | — | — | — | — | 1060 | 35 | 5800 | 230 |
| Control 11 | 99.5 | 0.5 | — | — | — | P | 0.9 | 5900 | 870 | 6100 | 900 |
| Control 12 | 60 | 40 | — | — | — | " | " | 25000 | 3300 | 26000 | 3900 |
| Control 13 | 80 | 20 | — | — | — | " | " | 2300 | 49 | 1900 | 240 |

TABLE 5-continued

| | COMPOSITION | | | | | SUPPORTING | AMOUNT | INITIAL | | 1,000 Hours After | |
|---|---|---|---|---|---|---|---|---|---|---|---|
| | ZnO | CaO | CoO | MgO | MnO | MATERIAL | (wt %) | $R_1$ (KΩ) | $R_2$ (KΩ) | $R_1'$ (KΩ) | $R_2'$ (KΩ) |
| Control 14 | " | — | — | 20 | — | " | " | 4600 | 95 | 7800 | 540 |

TABLE 6

| | COMPOSITION | | | | | BINDER | SHAPING PRESSURE (Kg/cm²) | SINTERING TEMPERATURE (°C.) | SINTERING TIME (hr) | SOLUTION | CONSISTENCY (wt %) | HEATING TEMPERATURE (°C.) |
|---|---|---|---|---|---|---|---|---|---|---|---|---|
| | ZnO | TiO₂ | SnO₂ | ZrO₂ | SiO₂ | | | | | | | |
| Example 34 | 70.4 | 29.6 | — | — | — | PVA | 1,000 | 1200 | 2 | Triethyl Phosphate | 18 | 500 |
| Example 35 | " | " | — | — | — | " | " | " | " | Ethyl Sulfide | 35 | " |
| Example 36 | 99.0 | 1.0 | — | — | — | " | " | " | " | Triethyl Phosphate | 18 | 500 |
| Example 37 | 80.3 | 19.7 | — | — | — | " | " | " | " | " | " | " |
| Example 38 | 60.4 | 39.6 | — | — | — | " | " | " | " | " | " | " |
| Example 39 | 55.7 | — | 44.3 | — | — | " | " | " | " | " | " | " |
| Example 40 | 60.7 | — | — | 39.3 | — | " | " | " | " | " | " | " |
| Example 41 | 76.0 | — | — | — | 24.0 | " | " | " | " | " | " | " |
| Example 42 | 64.7 | 18.2 | 17.1 | — | — | " | " | " | " | " | " | " |
| Example 43 | 54.1 | 8.9 | 16.7 | 13.6 | 6.7 | " | " | " | " | " | " | " |
| Example 44 | 55.7 | — | 44.3 | — | — | " | " | " | " | Ethyl Sulfide | 35 | " |
| Example 45 | 64.7 | 18.2 | 17.1 | — | — | " | " | " | " | " | " | " |
| Control 15 | 70.4 | 29.6 | — | — | — | " | " | " | " | — | — | — |
| Control 16 | 99.5 | 0.5 | — | — | — | " | " | " | " | Triethyl Phosphate | 18 | 500 |
| Control 17 | 30.4 | 69.6 | — | — | — | " | " | " | " | " | " | " |
| Control 18 | 70.4 | 29.6 | — | — | — | " | " | " | " | " | " | 700 |
| Control 19 | 64.7 | 18.2 | 17.1 | — | — | " | " | " | " | " | " | " |

TABLE 7

| | COMPOSITION | | | | | SUPPORTING | AMOUNT | INITIAL | | 1,000 Hours After | |
|---|---|---|---|---|---|---|---|---|---|---|---|
| | ZnO | TiO₂ | SnO₂ | ZrO₂ | SiO₂ | MATERIAL | (wt %) | $R_1$ (KΩ) | $R_2$ (KΩ) | $R_1'$ (KΩ) | $R_2'$ (KΩ) |
| Example 34 | 70 | 30 | — | — | — | P | 0.8 | 1900 | 60 | 1950 | 65 |
| Example 35 | " | " | — | — | — | S | 0.9 | 2200 | 80 | 2300 | 90 |
| Example 36 | 99 | 1 | — | — | — | P | 0.8 | 3200 | 210 | 3300 | 230 |
| Example 37 | 80 | 20 | — | — | — | " | " | 2500 | 105 | 2600 | 110 |
| Example 38 | 60 | 40 | — | — | — | " | " | 2100 | 120 | 2200 | 130 |
| Example 39 | 70 | — | 30 | — | — | " | " | " | 80 | " | 90 |
| Example 40 | " | — | — | 30 | — | " | " | 2400 | 90 | 2500 | 100 |
| Example 41 | " | — | — | — | 30 | " | " | 2900 | 140 | 2900 | 145 |
| Example 42 | " | 20 | 10 | — | — | " | " | 1800 | 45 | 1900 | 55 |
| Example 43 | 60 | 10 | " | 10 | 10 | " | " | 2300 | 100 | 2100 | 110 |
| Example 44 | 70 | — | 30 | — | — | S | " | 2600 | " | 2800 | " |
| Example 45 | " | 20 | 10 | — | — | " | " | 2100 | 80 | 2200 | 90 |
| Control 15 | " | 30 | — | — | — | — | | 1250 | 10 | 3400 | 135 |
| Control 16 | 99.5 | 0.5 | — | — | — | P | 0.8 | 4700 | 560 | 5000 | 570 |
| Control 17 | 30 | 70 | — | — | — | " | " | 3700 | 400 | 3800 | 420 |
| Control 18 | 70 | 30 | — | — | — | " | " | 1600 | 30 | 2900 | 90 |
| Control 19 | " | 20 | 10 | — | — | " | " | 1700 | 50 | 2800 | 120 |

TABLE 8

| | COMPOSITION | | | BINDER | SHAPING PRESSURE (Kg/cm²) | SINTERING TEMPERATURE (°C.) | SINTERING TIME (hr) | SOLUTION | CONSISTENCY (wt %) | HEATING TEMPERATURE (°C.) |
|---|---|---|---|---|---|---|---|---|---|---|
| | ZnO | WO₃ | MoO₃ | | | | | | | |
| Example 46 | 69.3 | — | 30.7 | PVA | 1,000 | 1000 | 1 | Triethyl Phosphate | 18 | 550 |
| Example 47 | " | " | " | " | " | " | " | Ethyl Sulfide | 35 | " |
| Example 48 | 83.6 | — | 16.4 | " | " | " | " | Triethyl Phosphate | 18 | 550 |
| Example 49 | 45.9 | — | 55.1 | " | " | " | " | " | " | " |
| Example 50 | 58.4 | 41.6 | — | " | " | " | " | " | " | " |
| Example 51 | 63.4 | 22.6 | 14.0 | " | " | " | " | " | " | " |
| Control 20 | 69.3 | — | 30.7 | " | " | " | " | — | — | — |
| Control 21 | 91.5 | — | 8.5 | " | " | " | " | Triethyl Phosphate | 18 | 550 |

TABLE 8-continued

| | COMPOSITION | | | BINDER | SHAPING PRESSURE (Kg/cm²) | SINTERING TEMPERATURE (°C.) | SINTERING TIME (hr) | SOLUTION | CONSISTENCY (wt %) | HEATING TEMPERATURE (°C.) |
|---|---|---|---|---|---|---|---|---|---|---|
| | ZnO | WO₃ | MoO₃ | | | | | | | |
| Control 22 | 40.9 | — | 59.1 | " | " | " | " | " | " | " |
| Control 23 | 69.3 | — | 30.7 | " | " | " | " | " | " | 700 |

TABLE 9

| | COMPOSITION | | | SUPPORTING MATERIAL | AMOUNT (wt %) | INITIAL | | 1,000 Hours After | |
|---|---|---|---|---|---|---|---|---|---|
| | ZnO | WO₂ | MoO₃ | | | R₁ (KΩ) | R₂ (KΩ) | R₁' (KΩ) | R₂' (KΩ) |
| Example 46 | 80 | — | 20 | P | 0.8 | 2700 | 160 | 2800 | 180 |
| Example 47 | " | — | " | S | 0.9 | 3000 | 140 | 3100 | 160 |
| Example 48 | 90 | — | 10 | P | 0.8 | 3400 | 290 | 3600 | 310 |
| Example 49 | 60 | — | 40 | " | " | 3700 | 340 | 3900 | 360 |
| Example 50 | 80 | 20 | — | " | " | 2400 | 210 | 2500 | 220 |
| Example 51 | " | 10 | 10 | " | " | 2600 | 190 | 2800 | 210 |
| Control 20 | " | — | 20 | — | — | 2200 | 100 | 6400 | 460 |
| Control 21 | 95 | — | 5 | P | 0.8 | 6700 | 850 | 6800 | 860 |
| Control 22 | 55 | — | 45 | " | " | 4400 | 560 | 4600 | 600 |
| Control 23 | 80 | — | 20 | " | " | 2500 | 130 | 4200 | 340 |

TABLE 10

| | COMPOSITION | | | BINDER | SHAPING PRESSURE (Kg/cm²) | SINTERING TEMPERATURE (°C.) | SINTERING TIME (hr) | SOLUTION | CONSISTENCY (wt %) | HEATING TEMPERATURE (°C.) |
|---|---|---|---|---|---|---|---|---|---|---|
| | ZnO | Cr₂O₃ | Fe₂O₃ | | | | | | | |
| Example 52 | 82.8 | 17.2 | — | PVA | 1000 | 1200 | 2 | Triethyl Phosphate | 18 | 550 |
| Example 53 | " | " | — | " | " | " | " | Ethyl Sulfide | 35 | " |
| Example 54 | 98.1 | 1.9 | — | " | " | " | " | Triethyl Phosphate | 18 | " |
| Example 55 | 44.5 | 55.5 | — | " | " | " | " | " | 20 | " |
| Example 56 | 67.1 | — | 22.9 | " | " | " | " | " | " | " |
| Example 57 | 67.6 | 15.8 | 16.6 | " | " | " | " | " | 16 | " |
| Example 58 | " | " | " | " | " | " | " | Diethyl Sulfide | 35 | " |
| Control 24 | 82.8 | 17.2 | — | " | " | " | " | — | — | — |
| Control 25 | 99.1 | 0.9 | — | " | " | " | " | Ethyl Sulfide | 18 | 550 |
| Control 26 | 39.6 | 60.4 | — | " | " | " | " | " | " | " |
| Control 27 | 82.8 | 17.2 | — | — | — | — | — | — | — | 700 |
| Control 28 | 67.6 | 15.8 | 16.6 | " | " | " | " | " | " | " |

TABLE 11

| | COMPOSITION | | | SUPPORTING MATERIAL | AMOUNT (wt %) | INITIAL | | 1,000 Hours After | |
|---|---|---|---|---|---|---|---|---|---|
| | ZnO | Cr₂O₃ | Fe₂O₃ | | | R₁ (KΩ) | R₂ (KΩ) | R'₁ (KΩ) | R'₂ (KΩ) |
| Example 52 | 90 | 10 | — | P | 0.8 | 2500 | 67 | 2600 | 72 |
| Example 53 | 90 | 10 | — | S | 0.9 | 2800 | 85 | 2900 | 100 |
| Example 54 | 99 | 1 | — | P | 0.8 | 3900 | 270 | 4300 | 310 |
| Example 55 | 60 | 40 | — | P | 0.7 | 3600 | 240 | 3700 | 270 |
| Example 56 | 80 | — | 20 | P | 0.8 | 3200 | 120 | 3300 | 135 |
| Example 57 | 80 | 10 | 10 | P | 0.8 | 2300 | 45 | 2400 | 50 |
| Example 58 | 80 | 10 | 10 | S | 0.8 | 2500 | 110 | 2600 | 120 |
| Control 24 | 90 | 10 | — | — | — | 1700 | 25 | 7300 | 185 |
| Control 25 | 99.5 | 0.5 | — | S | 0.8 | 5700 | 680 | 5900 | 730 |
| Control 26 | 55 | 45 | — | S | 0.8 | 4900 | 560 | 5000 | 580 |
| Control 27 | 90 | 10 | — | S | 0.7 | 2100 | 40 | 4200 | 320 |
| Control 28 | 80 | 10 | 10 | S | 0.7 | 1900 | 70 | 4500 | 390 |

TABLE 12

| | COMPOSITION | | BINDER | SHAPING PRESSURE (Kg/cm²) | SINTERING TEMPERATURE (°C.) | SINTERING TIME (hr) | SOLUTION | CONSISTENCY (wt %) | HEATING TEMPERATURE (°C.) |
|---|---|---|---|---|---|---|---|---|---|
| | ZnO | V₂O₃ | | | | | | | |
| Example 59 | 80.1 | 19.9 | PVA | 1,000 | 1100 | 0.5 | Triethyl Phosphate | 18 | 550 |
| Example 60 | 80.1 | 19.9 | " | " | " | " | Ethyl | 35 | |

TABLE 12-continued

|  | COMPOSITION | | BINDER | SHAPING PRESSURE (Kg/cm²) | SINTERING TEMPERATURE (°C.) | SINTERING TIME (hr) | SOLUTION | CONSISTENCY (wt %) | HEATING TEMPERATURE (°C.) |
| --- | --- | --- | --- | --- | --- | --- | --- | --- | --- |
|  | ZnO | V₂O₃ | | | | | | | |
| Example 61 | 89.5 | 10.5 | " | " | " | " | Sulfide Triethyl Phosphate | 18 | 500 |
| Example 62 | 71.7 | 28.3 | " | " | " | " | Triethyl Phosphate | 18 | 500 |
| Control 29 | 80.1 | 19.9 | " | " | " | " | — | — | — |
| Control 30 | 95.6 | 4.4 | " | " | " | " | Triethyl Phosphate | 18 | 500 |
| Control 31 | 64.1 | 35.9 | " | " | " | " | Triethyl Phosphate | 18 | 500 |
| Control 32 | 80.1 | 19.9 | " | " | " | " | Triethyl Phosphate | 18 | 700 |

TABLE 13

|  | COMPOSITION | | SUPPORTING MATERIAL | AMOUNT (wt %) | INITIAL | | 1,000 Hours After | |
| --- | --- | --- | --- | --- | --- | --- | --- | --- |
|  | ZnO | V₂O₅ | | | $R_1$ (KΩ) | $R_2$ (KΩ) | $R'_1$ (KΩ) | $R'_2$ (KΩ) |
| Example 59 | 90 | 10 | P | 0.8 | 3200 | 270 | 3200 | 280 |
| Example 60 | 90 | 10 | S | 0.9 | 3500 | 240 | 3600 | 240 |
| Example 61 | 95 | 5 | P | 0.8 | 5000 | 240 | 5100 | 250 |
| Example 62 | 85 | 15 | P | 0.8 | 4100 | 290 | 4200 | 310 |
| Control 29 | 90 | 10 | — | — | 3000 | 100 | 6300 | 290 |
| Control 30 | 98 | 2 | P | 0.8 | 8000 | 900 | 8000 | 950 |
| Control 31 | 80 | 20 | P | 0.8 | 7500 | 800 | 7700 | 830 |
| Control 32 | 90 | 10 | P | 0.8 | 3000 | 260 | 4000 | 650 |

TABLE 14

|  | COMPOSITION | | | | | | | | Binder | Shaping Pressure (Kg/cm²) | Sintering Temperature (°C.) | Sintering Time (hr) | Solution | Consistency (wt %) | Heating Temperature (°C.) |
| --- | --- | --- | --- | --- | --- | --- | --- | --- | --- | --- | --- | --- | --- | --- | --- |
|  | SnO₂ | MgO | CaO | CoO | MnO | SrO | NiO | CuO | | | | | | | |
| Example 63 | 89.0 | — | — | 11.0 | — | — | — | — | PVA | 1000 | 1200 | 2 | Triethyl Phosphate | 18 | 550 |
| Example 64 | 89.0 | — | — | 11.0 | — | — | — | — | " | " | " | " | Ethyl Sulfide | 35 | 550 |
| Example 65 | 99.95 | — | — | 0.05 | — | — | — | — | " | " | " | " | Triethyl Phosphate | 18 | 500 |
| Example 66 | 94.8 | — | — | 5.2 | — | — | — | — | " | " | " | " | Triethyl Phosphate | " | " |
| Example 67 | 75.1 | — | — | 24.9 | — | — | — | — | " | " | " | " | Triethyl Phosphate | " | " |
| Example 68 | 66.8 | — | — | 33.2 | — | — | — | — | " | " | " | " | Triethyl Phosphate | " | " |
| Example 69 | 90.8 | — | 3.8 | — | 5.4 | — | — | — | " | " | " | " | Triethyl Phosphate | " | " |
| Example 70 | 82.8 | 3.2 | — | — | — | 8.1 | 5.9 | — | " | " | " | " | Triethyl Phosphate | " | " |
| Example 71 | 83.7 | — | 4.0 | 5.9 | — | — | — | 6.4 | " | " | " | " | Triethyl Phosphate | " | " |
| Example 72 | 86.8 | — | — | — | 7.5 | — | 5.7 | — | " | " | " | " | Ethyl Sulfide | 35 | " |
| Example 73 | 90.6 | — | 3.8 | — | — | — | 5.6 | — | " | " | " | " | Ethyl Sulfide | " | " |
| Control 33 | 89.0 | — | — | 11.0 | — | — | — | — | " | " | " | " | — | — | — |
| Control 34 | 57.3 | — | — | 42.7 | — | — | — | — | " | " | " | " | Triethyl | 18 | 500 |

TABLE 14-continued

| | COMPOSITION | | | | | | | | Binder | Shaping Pressure (Kg/cm²) | Sintering Temperature (°C.) | Sintering Time (hr) | Solution | Consistency (wt %) | Heating Temperature (°C.) |
|---|---|---|---|---|---|---|---|---|---|---|---|---|---|---|---|
| | $SnO_2$ | MgO | CaO | CoO | MnO | SrO | NiO | CuO | | | | | | | |
| Control 35 | 89.0 | — | — | 11.0 | — | — | — | — | " | " | " | " | Phosphate Triethyl Phosphate | " | 700 |
| Control 36 | 83.7 | — | 4.0 | 5.9 | — | — | — | 6.4 | " | " | " | " | Triethyl Phosphate | " | " |

TABLE 15

| | COMPOSITION | | | | | | | | SUPPORTING MATERIAL | AMOUNT (wt %) | INITIAL | | 1,000 Hours After | |
|---|---|---|---|---|---|---|---|---|---|---|---|---|---|---|
| | $SnO_2$ | MgO | CaO | CoO | MnO | SrO | NiO | CuO | | | $R_1$ (KΩ) | $R_2$ (KΩ) | $R'_1$ (KΩ) | $R'_2$ (KΩ) |
| Example 63 | 80 | — | — | 20 | — | — | — | — | P | 0.8 | 920 | 25 | 940 | 30 |
| Example 64 | 80 | — | — | 20 | — | — | — | — | S | 0.9 | 1300 | 40 | 1400 | 50 |
| Example 65 | 99.9 | — | — | 0.1 | — | — | — | — | P | 0.7 | 1200 | 35 | 1300 | 40 |
| Example 66 | 90 | — | — | 10 | — | — | — | — | " | 0.8 | 960 | 30 | 980 | 40 |
| Example 67 | 60 | — | — | 40 | — | — | — | — | " | " | 1300 | 70 | 1400 | 80 |
| Example 68 | 50 | — | — | 50 | — | — | — | — | " | " | 2000 | 120 | 2200 | 140 |
| Example 69 | 80 | — | 10 | — | 10 | — | — | — | " | " | 970 | 30 | 980 | 40 |
| Example 70 | 70 | 10 | — | — | — | 10 | 10 | — | " | " | 1100 | 70 | 1200 | 80 |
| Example 71 | 70 | — | 10 | 10 | — | — | — | 10 | " | " | 1400 | 60 | 1500 | 80 |
| Example 72 | 80 | — | — | — | 10 | — | 10 | — | S | 0.9 | 1500 | 80 | 1600 | 90 |
| Example 73 | 80 | — | 10 | — | — | — | 10 | — | " | " | 1600 | 100 | 1700 | 110 |
| Control 33 | 80 | — | — | 20 | — | — | — | — | — | — | 810 | 20 | 2300 | 62 |
| Control 34 | 40 | — | — | 60 | — | — | — | — | P | 0.8 | 2900 | 340 | 3100 | 380 |
| Control 35 | 80 | — | — | 20 | — | — | — | — | " | " | 900 | 30 | 1500 | 90 |
| Control 36 | 70 | — | 10 | 10 | — | — | — | 10 | " | " | 1300 | 50 | 2700 | 210 |

TABLE 16

| | COMPOSITION | | | BINDER | SHAPING PRESSURE (Kg/cm²) | SINTERING (°C.) | SINTERING (hr) | SOLUTION | CONSISTENCY (wt %) | HEATING TEMPERATURE (°C.) |
|---|---|---|---|---|---|---|---|---|---|---|
| | $SnO_2$ | $WO_3$ | $MoO_3$ | | | | | | | |
| Example 74 | 85.4 | 14.6 | — | PVA | 1000 | 1200 | 2 | Triethyl Phosphate | 18 | 550 |
| Example 75 | 85.4 | 14.6 | — | " | " | " | " | Ethyl Sulfide | 35 | " |
| Example 76 | 99.8 | 0.2 | — | " | " | " | " | Triethyl Phosphate | 18 | " |
| Example 77 | 72.2 | 27.8 | — | " | " | " | " | Triethyl Phosphate | " | " |
| Example 78 | 60.3 | 39.7 | — | " | " | " | " | Triethyl Phosphate | " | " |
| Example 79 | 49.4 | 50.6 | — | " | " | " | " | Triethyl Phosphate | " | " |
| Example 80 | 90.4 | — | 9.6 | " | " | " | " | Triethyl Phosphate | " | " |
| Example 81 | 76.3 | 14.6 | 9.1 | " | " | " | " | Triethyl Phosphate | " | " |
| Example 82 | 90.4 | — | 9.6 | " | " | " | " | Ethyl Sulfide | 35 | " |
| Control 37 | 85.4 | 14.6 | — | " | " | " | " | — | — | — |
| Control 38 | 39.4 | 60.6 | — | " | " | " | " | Triethyl Phosphate | 18 | 550 |
| Control 39 | 85.4 | 14.6 | — | " | " | " | " | Triethyl Phosphate | " | 700 |
| Control 40 | 90.4 | — | 9.6 | " | " | " | " | Triethyl Phosphate | " | " |

TABLE 17

| | COMPOSITION | | | SUPPORTING MATERIAL | AMOUNT (wt %) | INITIAL | | 1,000 Hours After | |
|---|---|---|---|---|---|---|---|---|---|
| | $SnO_2$ | $WO_3$ | $MoO_3$ | | | $R_1$ (KΩ) | $R_2$ (KΩ) | $R'_1$ (KΩ) | $R'_2$ (KΩ) |
| Example 74 | 90 | 10 | — | P | 0.7 | 2800 | 105 | 2900 | 120 |
| Example 75 | 90 | 10 | — | S | 0.9 | 2900 | 70 | 3000 | 80 |
| Example 76 | 99.9 | 0.1 | — | P | 0.7 | 3700 | 190 | 3900 | 200 |

TABLE 17-continued

| | COMPOSITION | | | SUPPORTING | AMOUNT | INITIAL | | 1,000 Hours After | |
|---|---|---|---|---|---|---|---|---|---|
| | SnO₂ | WO₃ | MoO₃ | MATERIAL | (wt %) | R₁ (KΩ) | R₂ (KΩ) | R'₁ (KΩ) | R'₂ (KΩ) |
| Example 77 | 80 | 20 | — | " | " | 2300 | 70 | 2400 | 80 |
| Example 78 | 70 | 30 | — | " | " | 2500 | 90 | 2600 | 100 |
| Example 79 | 60 | 40 | — | " | " | 3000 | 140 | 3100 | 150 |
| Example 80 | 90 | — | 10 | " | " | 2200 | 90 | 2300 | 95 |
| Example 81 | 80 | 10 | 10 | " | " | 1700 | 55 | 1800 | 60 |
| Example 82 | 90 | — | 10 | S | " | 3100 | 80 | 3200 | 90 |
| Control 37 | 90 | 10 | — | — | — | 2100 | 86 | 3400 | 290 |
| Control 38 | 50 | 50 | — | P | — | 3400 | 390 | 3500 | 400 |
| Control 39 | 90 | 10 | — | " | — | 2400 | 80 | 3600 | 350 |
| Control 40 | 90 | — | 10 | " | — | 2600 | 140 | 3800 | 560 |

TABLE 18

| | Composition | | | | Binder | Shaping Pressure (Kg/cm²) | Sintering Temperature (°C.) | Sintering Time (hr) | Solution | Consistency (wt %) | Heating Temperature (°C.) |
|---|---|---|---|---|---|---|---|---|---|---|---|
| | SnO₂ | Al₂O₂ | Ga₂O₃ | In₂O₃ | | | | | | | |
| Example 83 | 76.4 | — | 23.6 | — | PVA | 1000 | 1200 | 12 | Triethyl Phosphate | 18 | 500 |
| Example 84 | 76.4 | — | 23.6 | — | " | " | " | " | Ethyl Sulfide | 35 | 500 |
| Example 85 | 99.9 | — | 0.1 | — | " | " | " | " | Triethyl Phosphate | 18 | " |
| Example 86 | 79.0 | — | 21.0 | — | " | " | " | " | Triethyl Phosphate | " | " |
| Example 87 | 65.3 | — | 44.7 | — | " | " | " | " | Triethyl Phosphate | " | " |
| Example 88 | 54.8 | — | 45.2 | — | " | " | " | " | Triethyl Phosphate | " | " |
| Example 89 | 68.5 | — | — | 31.5 | " | 800 | " | " | Triethyl Phosphate | " | " |
| Example 90 | 80.7 | 6.8 | 12.5 | — | " | " | " | " | Triethyl Phosphate | " | " |
| Example 91 | 64.5 | 6.4 | 11.7 | 17.4 | " | 1000 | " | " | Ethyl Sulfide | 35 | " |
| Control 41 | 76.4 | — | 23.6 | — | " | " | " | " | — | — | — |
| Control 42 | 44.6 | — | 55.4 | — | " | " | " | " | Triethyl Phosphate | 18 | 500 |
| Control 43 | 76.4 | — | 23.6 | — | " | " | " | " | Triethyl Phosphate | " | 700 |
| Control 44 | 68.5 | — | — | 31.5 | " | " | " | " | Triethyl Phosphate | " | " |

TABLE 19

| | COMPOSITION | | | | SUPPORTING | AMOUNT | INITIAL | | 1,000 Hours After | |
|---|---|---|---|---|---|---|---|---|---|---|
| | SnO₂ | Al₂O₃ | Ga₂O₃ | In₂O₃ | MATERIAL | (wt %) | R₁ (KΩ) | R₂ (KΩ) | R'₁ (KΩ) | R'₂ (KΩ) |
| Example 83 | 80 | — | 20 | — | P | 0.7 | 2200 | 65 | 2400 | 80 |
| Example 84 | 80 | — | 20 | — | S | 1.1 | 2800 | 70 | 3000 | 80 |
| Example 85 | 99.9 | — | 0.1 | — | P | 1.6 | 3400 | 95 | 3500 | 110 |
| Example 86 | 90 | — | 10 | — | " | 1.2 | 2700 | 80 | 2900 | 100 |
| Example 87 | 70 | — | 30 | — | " | 0.6 | 1300 | 40 | 1400 | 50 |
| Example 88 | 60 | — | 40 | — | " | 0.5 | 980 | 60 | 990 | 65 |
| Example 89 | 80 | — | — | 20 | " | 0.5 | 2900 | 90 | 3000 | 100 |
| Example 90 | 80 | 10 | 10 | — | " | 0.9 | 3200 | 80 | 3300 | 90 |
| Example 91 | 70 | 10 | 10 | 10 | S | 1.5 | 3400 | 100 | 3500 | 120 |
| Control 41 | 80 | — | 20 | — | — | — | 1700 | 20 | 6600 | 250 |
| Control 42 | 50 | — | 50 | — | P | 0.5 | 300 | 90 | 310 | 115 |
| Control 43 | 80 | — | 20 | — | " | 0.6 | 2100 | 45 | 1100 | 250 |
| Control 44 | 80 | — | — | 20 | " | 0.7 | 2500 | 70 | 5100 | 310 |

TABLE 20

| | COMPOSITION | | | | BINDER | SHAPING PRESSURE (Kg/cm²) | SINTERING TEMPERATURE (°C.) | SINTERING TIME (hr) | SOLUTION | CONSISTENCY (wt %) | HEATING TEMPERATURE (°C.) |
|---|---|---|---|---|---|---|---|---|---|---|---|
| | SnO₂ | V₂O₅ | Nb₂O₅ | Ta₂O₅ | | | | | | | |
| Example 92 | 88.2 | 11.8 | — | — | PVA | 1000 | 1200 | 2 | Triethyl Phosphate | 18 | 550 |
| Example 93 | " | " | — | — | " | " | " | " | Ethyl | 35 | " |

TABLE 20-continued

| | COMPOSITION | | | | BINDER | SHAPING PRESSURE (Kg/cm²) | SINTERING TEMPERATURE (°C.) | SINTERING TIME (hr) | SOLUTION | CONSISTENCY (wt %) | HEATING TEMPERATURE (°C.) |
|---|---|---|---|---|---|---|---|---|---|---|---|
| | $SnO_2$ | $V_2O_5$ | $Nb_2O_5$ | $Ta_2O_5$ | | | | | | | |
| Example 94 | 99.9 | 0.1 | — | — | " | " | " | " | Sulfide Triethyl Phosphate | 18 | 550 |
| Example 95 | 76.8 | 23.2 | — | — | " | " | " | " | Triethyl Phosphate | " | " |
| Example 96 | 71.3 | 28.7 | — | — | " | " | " | " | Triethyl Phosphate | " | " |
| Example 97 | 83.6 | — | 16.4 | — | " | " | " | " | Triethyl Phosphate | " | " |
| Example 98 | 75.5 | — | — | 24.5 | " | " | " | " | Triethyl Phosphate | " | " |
| Example 99 | 72.9 | 11.0 | 16.1 | — | " | " | " | " | Triethyl Phosphate | " | " |
| Control 45 | 88.2 | 11.8 | — | — | " | " | " | " | — | — | — |
| Control 46 | 65.9 | 34.1 | — | — | " | " | " | " | Triethyl Phosphate | 18 | 550 |
| Control 47 | 88.2 | 11.8 | — | — | " | " | " | " | Triethyl Phosphate | " | 700 |
| Control 48 | 83.6 | — | 16.4 | — | " | " | " | " | Triethyl Phosphate | " | " |

TABLE 21

| | COMPOSITION | | | | SUPPORTING MATERIAL | AMOUNT (wt %) | INITIAL | | 1,000 Hours After | |
|---|---|---|---|---|---|---|---|---|---|---|
| | $SnO_2$ | $V_2O_5$ | $Nb_2O_5$ | $Ta_2O_5$ | | | $R_1$ (KΩ) | $R_2$ (KΩ) | $R'_1$ (KΩ) | $R'_2$ (KΩ) |
| Example 92 | 90 | 10 | — | — | P | 0.6 | 2000 | 80 | 2200 | 90 |
| Example 93 | 90 | 10 | — | — | S | 1.0 | 4900 | 87 | 5100 | 91 |
| Example 94 | 99.9 | 0.1 | — | — | P | 1.2 | 1700 | 50 | 1800 | 60 |
| Example 95 | 80 | 20 | — | — | P | 0.5 | 2800 | 140 | 2900 | 150 |
| Example 96 | 75 | 25 | — | — | P | 0.4 | 3700 | 230 | 3900 | 250 |
| Example 97 | 90 | — | 10 | — | P | 0.8 | 2400 | 90 | 2500 | 110 |
| Example 98 | 90 | — | — | 10 | P | 1.0 | 2300 | 110 | 2400 | 120 |
| Example 99 | 80 | 10 | 10 | — | P | 0.7 | 3100 | 240 | 3200 | 260 |
| Control 45 | 90 | 10 | — | — | — | — | 1600 | 27 | 2900 | 180 |
| Control 46 | 70 | 30 | — | — | P | 0.4 | 4400 | 580 | 4600 | 600 |
| Control 47 | 90 | 10 | — | — | P | 0.6 | 1800 | 70 | 3900 | 240 |
| Control 48 | 90 | — | 10 | — | P | 0.8 | 2100 | 90 | 3800 | 230 |

TABLE 22

| | COMPOSITION | | | | | BINDER | SHAPING PRESSURE (Kg/cm²) | SINTERING TEMPERATURE (°C.) | SINTERING TIME (hr) | SOLUTION | CONSISTENCY (wt %) | HEATING TEMPERATURE (°C.) |
|---|---|---|---|---|---|---|---|---|---|---|---|---|
| | $Cr_2O_3$ | MgO | NiO | CoO | MnO | | | | | | | |
| Example 100 | 82.7 | — | 17.3 | — | — | PVA | 1000 | 1300 | 2 | Triethyl Phosphate | 18 | 550 |
| Example 101 | 82.7 | — | 17.3 | — | — | " | 1000 | " | " | Ethyl Sulfide | 35 | 550 |
| Example 102 | 89.1 | — | 10.9 | — | — | " | 2000 | " | " | Triethyl Phosphate | 18 | 550 |
| Example 103 | 67.0 | — | 33.0 | — | — | " | 500 | " | " | Triethyl Phosphate | 9 | 550 |
| Example 104 | 46.5 | — | 53.5 | — | — | " | 1000 | " | " | Triethyl Phosphate | 18 | 550 |
| Example 105 | 89.8 | 10.2 | — | — | — | " | 1500 | " | " | Triethyl Phosphate | 18 | 550 |
| Example 106 | 82.5 | — | — | 17.5 | — | " | 1000 | " | " | Triethyl Phosphate | 18 | 550 |
| Example 107 | 82.9 | — | 11.6 | — | 5.5 | " | 1000 | " | " | Triethyl Phosphate | 18 | 550 |
| Example 108 | 89.8 | 10.2 | — | — | — | " | 2000 | " | " | Diethyl Sulfide | 35 | 550 |
| Control 49 | 82.7 | — | 17.3 | — | — | " | 1000 | " | " | — | — | — |
| Control 50 | 94.8 | — | 5.2 | — | — | " | 2000 | " | " | Triethyl Phosphate | 18 | 550 |
| Control 51 | 33.7 | — | 66.3 | — | — | " | 800 | " | " | Triethyl Phosphate | 18 | 550 |
| Control 52 | 82.6 | — | 17.4 | — | — | " | 1000 | " | " | Triethyl Phosphate | 18 | 700 |
| Control 53 | 82.5 | — | — | 17.5 | — | " | 1000 | " | " | Triethyl | 18 | 700 |

TABLE 22-continued

| | COMPOSITION | | | | | BINDER | SHAPING PRESSURE (Kg/cm²) | SINTERING TEMPERATURE (°C.) | SINTERING TIME (hr) | SOLUTION | CONSISTENCY (wt %) | HEATING TEMPERATURE (°C.) |
|---|---|---|---|---|---|---|---|---|---|---|---|---|
| | $Cr_2O_3$ | MgO | NiO | CoO | MnO | | | | | | | |
| | | | | | | | | | | Phosphate | | |

TABLE 23

| | COMPOSITION | | | | | SUPPORTING MATERIAL | AMOUNT (wt %) | INITIAL | | 1,000 Hours After | |
|---|---|---|---|---|---|---|---|---|---|---|---|
| | $Cr_2O_3$ | MgO | NiO | CoO | MnO | | | $R_1$ (KΩ) | $R_2$ (KΩ) | $R'_1$ (KΩ) | $R'_2$ (KΩ) |
| Example 100 | 70 | — | 30 | — | — | P | 0.8 | 2900 | 35 | 3100 | 45 |
| Example 101 | 70 | — | 30 | — | — | S | 1.2 | 3400 | 60 | 3500 | 70 |
| Example 102 | 80 | — | 20 | — | — | P | 0.7 | 4700 | 190 | 4900 | 200 |
| Example 103 | 50 | — | 50 | — | — | P | 0.1 | 3200 | 60 | 3300 | 80 |
| Example 104 | 30 | — | 70 | — | — | P | 0.6 | 3400 | 170 | 3600 | 180 |
| Example 105 | 70 | 30 | — | — | — | P | 2.0 | 3200 | 40 | 3400 | 50 |
| Example 106 | 70 | — | — | 30 | — | P | 1.5 | 3400 | 60 | 3500 | 80 |
| Example 107 | 70 | — | 20 | — | 10 | P | 1.2 | 3200 | 45 | 3300 | 60 |
| Example 108 | 70 | 30 | — | — | — | S | 2.0 | 3600 | 90 | 3800 | 100 |
| Control 49 | 70 | — | 30 | — | — | — | — | 1900 | 13 | 3400 | 150 |
| Control 50 | 90 | — | 10 | — | — | P | 0.3 | 8900 | 560 | 9200 | 600 |
| Control 51 | 20 | — | 80 | — | — | P | 0.6 | 3800 | 420 | 3900 | 430 |
| Control 52 | 70 | — | 30 | — | — | P | 1.0 | 2600 | 30 | 5100 | 150 |
| Control 53 | 70 | — | — | 30 | — | P | 1.8 | 3100 | 45 | 3200 | 60 |

TABLE 24

| | COMPOSITION | | | | | BINDER | SHAPING PRESSURE (Kg/cm²) | SINTERING TEMPERATURE (°C.) | SINTERING TIME (hr) | SOLUTION | CONSISTENCY (wt %) | HEATING TEMPERATURE (°C.) |
|---|---|---|---|---|---|---|---|---|---|---|---|---|
| | $Cr_2O_3$ | $TiO_2$ | $SnO_2$ | $ZrO_2$ | $SiO_2$ | | | | | | | |
| Example 109 | 60.2 | — | 39.8 | — | — | PVA | 1,000 | 1300 | 2 | Triethyl Phosphate | 18 | 550 |
| Example 110 | 60.2 | — | 39.8 | — | — | ″ | ″ | ″ | ″ | Ethyl Sulfide | 35 | 550 |
| Example 111 | 80.1 | — | 19.9 | — | — | ″ | ″ | ″ | ″ | Triethyl Phosphate | 18 | 550 |
| Example 112 | 40.2 | — | 59.8 | — | — | ″ | ″ | ″ | ″ | Triethyl Phosphate | 18 | 550 |
| Example 113 | 74.0 | 26.0 | — | — | — | ″ | ″ | ″ | ″ | Triethyl Phosphate | 18 | 550 |
| Example 114 | 62.5 | — | 20.7 | 16.8 | — | ″ | ″ | ″ | ″ | Triethyl Phosphate | 18 | 550 |
| Example 115 | 68.4 | — | 22.6 | — | 9.0 | ″ | ″ | ″ | ″ | Triethyl Phosphate | 18 | 550 |
| Example 116 | 74.0 | 26.0 | — | — | — | ″ | ″ | ″ | ″ | Ethyl Sulfide | 35 | 550 |
| Control 54 | 60.2 | — | 39.8 | — | — | ″ | ″ | ″ | ″ | — | — | — |
| Control 55 | 90.1 | — | 9.9 | — | — | ″ | ″ | ″ | ″ | Triethyl Phosphate | 18 | 550 |
| Control 56 | 30.1 | — | 69.9 | — | — | ″ | ″ | ″ | ″ | Triethyl Phosphate | 18 | 550 |
| Control 57 | 60.2 | — | 39.8 | — | — | ″ | ″ | ″ | ″ | Triethyl Phosphate | 18 | 700 |
| Control 58 | 74.0 | 26.0 | — | — | — | ″ | ″ | ″ | ″ | Triethyl Phosphate | 18 | 700 |

TABLE 25

| | COMPOSITION | | | | | SUPPORTING MATERIAL | AMOUNT (wt %) | INITIAL | | 1,000 Hours After | |
|---|---|---|---|---|---|---|---|---|---|---|---|
| | $Cr_2O_3$ | $TiO_2$ | $SnO_2$ | $ZrO_2$ | $SiO_2$ | | | $R_1$ (KΩ) | $R_2$ (KΩ) | $R'_{11}$ (KΩ) | $R'_2$ (KΩ) |
| Example 109 | 60 | — | 40 | — | — | P | 0.7 | 3500 | 120 | 3600 | 130 |
| Example 110 | 60 | — | 40 | — | — | S | 0.8 | 3800 | 200 | 4000 | 210 |
| Example 111 | 80 | — | 20 | — | — | P | 0.7 | 4400 | 190 | 4600 | 220 |
| Example 112 | 40 | — | 60 | — | — | P | 0.7 | 2900 | 170 | 3100 | 180 |
| Example 113 | 60 | 40 | — | — | — | P | 0.7 | 4000 | 180 | 4100 | 200 |
| Example 114 | 60 | — | 20 | 20 | — | P | 0.7 | 3200 | 140 | 3300 | 150 |
| Example 115 | 60 | — | 20 | — | 20 | P | 0.7 | 2900 | 170 | 3100 | 190 |
| Example 116 | 60 | 40 | — | — | — | S | 0.8 | 4100 | 160 | 4200 | 170 |
| Control 54 | 60 | — | 40 | — | — | — | — | 1700 | 80 | 6400 | 460 |
| Control 55 | 90 | — | 10 | — | — | P | 0.7 | 8900 | 670 | 9200 | 690 |
| Control 56 | 30 | — | 70 | — | — | P | 0.7 | 3400 | 360 | 3600 | 380 |
| Control 57 | 60 | — | 40 | — | — | P | 0.7 | 2200 | 100 | 4900 | 620 |

TABLE 25-continued

| | COMPOSITION | | | | | SUPPORTING | AMOUNT | INITIAL | | 1,000 Hours After | |
|---|---|---|---|---|---|---|---|---|---|---|---|
| | $Cr_2O_3$ | $TiO_2$ | $SnO_2$ | $ZrO_2$ | $SiO_2$ | MATERIAL | (wt %) | $R_1$ (KΩ) | $R_2$ (KΩ) | $R'_1$ (KΩ) | $R'_2$ (KΩ) |
| Control 58 | 60 | 40 | — | — | — | P | 0.7 | 3000 | 105 | 5300 | 450 |

TABLE 26

| | COMPOSITION | | | BINDER | SHAPING PRESSURE (Kg/cm²) | SINTERING TEMPERATURE (°C.) | SINTERING TIME (hr) | SOLUTION | CONSISTENCY (wt %) | HEATING TEMPERATURE (°C.) |
|---|---|---|---|---|---|---|---|---|---|---|
| | $Cr_2O_3$ | $WO_3$ | $MoO_3$ | | | | | | | |
| Example 117 | 72.4 | 27.6 | — | PVA | 1,000 | 1200 | 2 | Triethyl Phosphate | 18 | 550 |
| Example 118 | 72.4 | 27.6 | — | " | " | " | " | Ethyl Sulfide | 35 | 550 |
| Example 119 | 85.5 | 14.5 | — | " | " | " | " | Triethyl Phosphate | 18 | 550 |
| Example 120 | 60.5 | 39.5 | — | " | " | " | " | Triethyl Phosphate | 18 | 550 |
| Example 121 | 49.6 | 50.4 | — | " | " | " | " | Triethyl Phosphate | 20 | 550 |
| Example 122 | 80.9 | — | 19.1 | " | " | " | " | Triethyl Phosphate | 20 | 550 |
| Example 123 | 76.4 | 14.6 | 9.0 | " | " | " | " | Triethyl Phosphate | 20 | 550 |
| Example 124 | 80.9 | — | 19.1 | " | " | " | " | Ethyl Sulfide | 35 | 550 |
| Control 59 | 72.4 | 27.6 | — | " | " | " | " | — | — | — |
| Control 60 | 92.6 | 7.4 | — | " | " | " | " | Triethyl Phosphate | 18 | 550 |
| Control 61 | 39.6 | 60.4 | — | " | " | " | " | Triethyl Phosphate | 18 | 550 |
| Control 62 | 72.4 | 27.6 | — | " | " | " | " | Triethyl Phosphate | 18 | 700 |
| Control 63 | 80.9 | — | 19.1 | " | " | " | " | Triethyl Phosphate | 18 | 700 |

TABLE 27

| | COMPOSITION | | | SUPPORTING MATERIAL | AMOUNT (wt %) | INITIAL | | 1,000 Hours After | |
|---|---|---|---|---|---|---|---|---|---|
| | $Cr_2O_3$ | $WO_3$ | $MoO_3$ | | | $R_1$ (KΩ) | $R_2$ (KΩ) | $R'_1$ (KΩ) | $R'_2$ (KΩ) |
| Example 117 | 80 | 20 | — | P | 0.8 | 1800 | 60 | 1900 | 75 |
| Example 118 | 80 | 20 | — | S | 0.9 | 2300 | 105 | 2400 | 120 |
| Example 119 | 90 | 10 | — | P | 0.8 | 2700 | 95 | 2800 | 100 |
| Example 120 | 70 | 30 | — | P | 0.7 | 2200 | 110 | 2300 | 120 |
| Example 121 | 60 | 40 | — | P | 0.7 | 3400 | 210 | 3600 | 220 |
| Example 122 | 80 | — | 20 | P | 0.8 | 1900 | 90 | 2100 | 100 |
| Example 123 | 80 | 10 | 10 | P | 0.8 | 2000 | 70 | 2100 | 90 |
| Example 124 | 80 | — | 20 | S | 0.8 | 2500 | 120 | 2600 | 130 |
| Control 59 | 80 | 20 | — | — | — | 1000 | 23 | 2900 | 210 |
| Control 60 | 95 | 5 | — | P | 0.8 | 6700 | 450 | 6800 | 170 |
| Control 61 | 50 | 50 | — | P | 0.6 | 4800 | 480 | 5000 | 490 |
| Control 62 | 80 | 20 | — | P | 0.8 | 1700 | 45 | 3000 | 230 |
| Control 63 | 80 | — | 20 | P | 0.8 | 2200 | 80 | 1700 | 310 |

TABLE 28

| | COMPOSITION | | | | BINDER | SHAPING PRESSURE (Kg/cm²) | SINTERING TEMPERATURE (°C.) | SINTERING TIME (hr) | SOLUTION | CONSISTENCY (wt %) | HEATING TEMPERATURE (°C.) |
|---|---|---|---|---|---|---|---|---|---|---|---|
| | $Cr_2O_3$ | $V_2O_5$ | $Nb_2O_5$ | $Ta_2O_5$ | | | | | | | |
| Example 125 | 77.0 | 23.0 | — | — | PVA | 1,000 | 1200 | 2 | Triethyl Phosphate | 18 | 550 |
| Example 126 | 77.0 | 23.0 | — | — | " | " | " | " | Ethyl Sulfide | 35 | 550 |
| Example 127 | 88.3 | 11.7 | — | — | " | " | " | " | Triethyl Phosphate | 18 | 500 |
| Example 128 | 66.1 | 33.9 | — | — | " | " | " | " | Triethyl Phosphate | 20 | 500 |
| Example 129 | 69.6 | — | 30.4 | — | " | " | " | " | Triethyl Phosphate | 20 | 500 |
| Example 130 | 57.9 | — | — | 42.1 | " | " | " | " | Triethyl Phosphate | 20 | 500 |
| Example 131 | 73.1 | 10.9 | 16.0 | — | " | " | " | " | Triethyl Phosphate | 20 | 500 |
| Example 132 | 67.2 | 10.1 | — | 22.7 | " | " | " | " | Ethyl Sulfide | 18 | 500 |

TABLE 28-continued

| | COMPOSITION | | | | BIND-ER | SHAPING PRESSURE (Kg/cm²) | SINTERING TEMPERATURE (°C.) | SINTERING TIME (hr) | SOLUTION | CONSISTENCY (wt %) | HEATING TEMPERATURE (°C.) |
|---|---|---|---|---|---|---|---|---|---|---|---|
| | $Cr_2O_3$ | $V_2O_5$ | $Nb_2O_5$ | $Ta_2O_5$ | | | | | | | |
| Control 64 | 77.0 | 23.0 | — | — | " | " | " | " | — | — | — |
| Control 65 | 94.1 | 5.9 | — | — | " | " | " | " | Triethyl Phosphate | 18 | 500 |
| Control 66 | 55.6 | 44.4 | — | — | " | " | " | " | Triethyl Phosphate | 18 | 500 |
| Control 67 | 77.0 | 23.0 | — | — | " | " | " | " | Triethyl Phosphate | 18 | 700 |

TABLE 29

| | COMPOSITION | | | | SUPPORTING MATERIAL | AMOUNT (wt %) | INITIAL | | 1,000 Hours After | |
|---|---|---|---|---|---|---|---|---|---|---|
| | $Cr_2O_3$ | $V_2O_5$ | $Nb_2O_5$ | $Ta_2O_5$ | | | $R_1$ (KΩ) | $R_2$ (KΩ) | $R'_1$ (KΩ) | $R'_2$ (KΩ) |
| Example 125 | 80 | 20 | — | — | P | 0.8 | 3200 | 100 | 3300 | 110 |
| Example 126 | 80 | 20 | — | — | S | 0.8 | 3400 | 95 | 3500 | 110 |
| Example 127 | 90 | 10 | — | — | P | 0.7 | 4900 | 130 | 5000 | 150 |
| Example 128 | 70 | 30 | — | — | P | 0.7 | 2900 | 140 | 3000 | 150 |
| Example 129 | 80 | — | 20 | — | P | 0.7 | 3100 | 130 | 3200 | 140 |
| Example 130 | 80 | — | — | 20 | P | 0.7 | 2700 | 120 | 2800 | 130 |
| Example 131 | 80 | 10 | 10 | — | P | 0.7 | 3100 | 130 | 320 | 140 |
| Example 132 | 80 | 10 | — | 10 | S | 0.7 | 3300 | 170 | 3400 | 180 |
| Control 64 | 80 | 20 | — | — | — | — | 2100 | 71 | 8200 | 210 |
| Control 65 | 95 | 5 | — | — | P | 0.7 | 9300 | 940 | 9500 | 960 |
| Control 66 | 60 | 40 | — | — | P | 0.7 | 3900 | 410 | 4000 | 440 |
| Control 67 | 80 | 20 | — | — | P | 0.7 | 2900 | 80 | 5700 | 370 |

What is claimed is:

1. A moisture sensitive element comprising:
   a porous metal oxide ceramic; and
   at least one of phosphorus and sulfur in at least one of a pure and oxide form, said at least one of phosphorus and sulfur being supported by said porous metal oxide ceramic.

2. A moisture sensitive element according to claim 1, wherein the elemental amount of said at least one of phosphorus and sulfur is about 0.1 to about 2.0 weight percent.

3. A moisture sensitive element according to claim 1, wherein said phosphorus and sulfur are both supported by said porous metal oxide ceramic, and the added amount of the combination of said phosphorus and sulfur is about 0.1 to about 2.0 weight percent.

4. A moisture sensitive element according to claim 1 or 2, wherein the porous metal oxide ceramic is the metal oxide selected from the group consisting of ZnO, $Fe_2O_3$, $SnO_2$, $Cr_2O_3$, $Fe_3O_4$, $MgO.Cr_2O_3$, $BaO.TiO_2$ and $MnO.Fe_2O_3$.

5. A moisture sensitive element according to claim 1 or 2, wherein the porous metal oxide ceramic comprises about 70 to about 99 mole percent of ZnO and about 1 to about 30 mole percent of at least one metal oxide selected from the group consisting of MgO, CaO, CoO, and MnO.

6. A moisture sensitive element according to claim 1 or 2, wherein the porous metal oxide ceramic comprises about 40 to about 99 mole percent of ZnO, and about 1 to about 60 mole percent of at least one metal oxide selected from the group consisting of $TiO_2$, $SnO_2$, $ZrO_2$ and $SiO_2$.

7. A moisture sensitive element according to claim 1 or 2, wherein the porous metal oxide ceramics comprises about 60 to about 90 mole percent of ZnO and about 10 to about 40 mole percent of at least one either $WO_3$ or $MoO_3$.

8. A moisture sensitive element according to claim 1 or 2, wherein the porous metal oxide ceramic comprises about 60 to about 99 mole percent of ZnO and about 1 to about 40 mole percent of at least either $Cr_2O_3$ or $Fe_2O_3$.

9. A moisture sensitive element according to claim 1 or 2, wherein the porous metal oxide ceramic comprises about 85 to about 95 mole percent of ZnO and about 5 to about 15 mole percent of $V_2O_5$.

10. A moisture sensitive element according to claim 1 or 2, wherein the porous metal oxide ceramic comprises about 50 to about 99.9 mole percent of $SnO_2$ and about 0.1 to about 50 mole percent of at least one metal oxide selected from the group consisting of MgO, CaO, CoO, MnO, SrO, NiO and CuO.

11. A moisture sensitive element according to claims 1 or 2, wherein the porous metal oxide ceramic comprises about 60 to about 99.9 mole percent of $SnO_2$ and about 0.1 to about 40 mole percent of at least either $WO_3$ or $MoO_3$.

12. A moisture sensitive element according to claim 1 or 2, wherein the porous metal oxide ceramic comprises about 60 to about 99.9 mole percent of $SnO_2$ and about 0.1 to about 40 mole percent of at least one metal oxide selected from the group consisting of $Al_2O_3$, $Ga_2O_3$, and $In_2O_3$.

13. A moisture sensitive element according to claim 1 or 2, wherein the porous metal oxide ceramics comprises about 75 to about 99.9 mole percent of $SnO_2$ and about 0.1 to about 25 mole percent of at least one metal oxide selected from the group consisting of $V_2O_5$, $Nb_2O_5$ and $Ta_2O_5$.

14. A moisture sensitive element according to claim 1 or 2, wherein the porous metal oxide ceramic comprises about 30 to about 80 mole percent of $Cr_2O_3$ and about 20 to about 70 mole percent of at least one metal oxide selected from the group consisting of MgO, NiO, CoO and MnO.

15. A moisture sensitive element according to claim 1 or 2, wherein the porous metal oxide ceramic comprises about 40 to about 80 mole percent of $Cr_2O_3$ and about 20 to about 60 mole percent of at least one metal oxide selected from the group consisting of $TiO_2$, $SnO_2$, $ZrO_2$ and $SiO_2$.

16. A moisture sensitive element according to claim 1 or 2, wherein the porous metal oxide ceramic comprises about 60 to about 90 mole percent of $Cr_2O_3$ and about 10 to about 30 mole percent of at least one of $WO_3$ and $MoO_3$.

17. A moisture sensitive element according to claim 1 or 2, wherein the porous metal oxide ceramic comprises about 70 to about 90 moler percent of $Cr_2O_3$ and about 10 to about 30 mole percent of at least one metal oxide selected from the group consisting of $V_2O_5$, $Nb_2O_5$ and $Ta_2O_5$.

* * * * *